(12) United States Patent
Edgren et al.

(10) Patent No.: US 6,797,283 B1
(45) Date of Patent: Sep. 28, 2004

(54) GASTRIC RETENTION DOSAGE FORM HAVING MULTIPLE LAYERS

(75) Inventors: David E. Edgren, Los Altos, CA (US); Francisco Jao, San Jose, CA (US); Patrick S. -L. Wong, Burlingame, CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 09/469,399

(22) Filed: Dec. 22, 1999

Related U.S. Application Data

(60) Provisional application No. 60/113,560, filed on Dec. 23, 1998.

(51) Int. Cl.[7] .............................. A61K 9/24; A61K 9/22; A61K 31/00; A61K 47/00
(52) U.S. Cl. ....................... 424/472; 424/465; 424/468; 424/469; 424/484; 424/485; 424/487; 424/488; 424/DIG. 6; 514/836; 514/866; 514/884; 514/909; 514/960; 514/961; 514/965
(58) Field of Search .................................. 424/457, 465, 424/468, 469, 470, 472, 473, 484, 485, 487, 488, DIG. 6; 514/152, 263.38, 315, 365, 369, 370, 371, 400, 401, 423, 428, 431, 449, 471, 634, 635, 646, 676, 688, 769, 770, 772, 772.3, 772.4, 772.5, 772.6, 772.7, 777, 778, 779, 781, 782, 784, 785, 786, 836, 866, 884, 909, 960, 961, 965; D24/100, 101, 102

(56) References Cited

U.S. PATENT DOCUMENTS

| | | | |
|---|---|---|---|
| 3,845,770 A | 11/1974 | Theeuwes et al. | 128/260 |
| 3,995,631 A | 12/1976 | Higuchi et al. | 128/260 |
| 4,034,756 A | 7/1977 | Higuchi et al. | 128/260 |
| 4,111,202 A | 9/1978 | Theeuwes | 128/260 |
| 4,290,426 A | 9/1981 | Luschen et al. | 128/260 |
| 4,320,759 A | 3/1982 | Theeuwes | 128/260 |
| 4,327,725 A | 5/1982 | Cortese et al. | 128/260 |
| 4,449,983 A | 5/1984 | Cortese et al. | 604/892 |
| 4,765,989 A | 8/1988 | Wong et al. | 424/473 |
| 4,767,627 A | 8/1988 | Caldwell et al. | 424/426 |
| 4,839,177 A | 6/1989 | Colombo et al. | 424/482 |
| 4,851,232 A | 7/1989 | Urquhart et al. | 424/469 |
| 4,871,548 A | 10/1989 | Edgren et al. | 424/488 |
| 4,892,778 A | 1/1990 | Theeuwes et al. | 428/218 |
| 4,915,949 A | 4/1990 | Wong et al. | 424/438 |
| 4,940,465 A | 7/1990 | Theeuwes et al. | 604/892.1 |
| 5,007,790 A | 4/1991 | Shell | 424/451 |
| 5,126,142 A | 6/1992 | Ayer et al. | 424/438 |
| 5,256,440 A | 10/1993 | Appel et al. | 427/3 |
| 5,443,843 A | 8/1995 | Curatolo et al. | 424/434 |
| 5,534,263 A | 7/1996 | Wong et al. | 424/473 |
| 5,582,837 A | 12/1996 | Shell | 424/451 |
| 5,780,057 A | 7/1998 | Conte et al. | 424/468 |
| 6,120,802 A | * 9/2000 | Breitenbach et al. | 424/464 |
| 6,120,803 A | * 9/2000 | Wong et al. | 424/473 |

FOREIGN PATENT DOCUMENTS

| | | |
|---|---|---|
| EP | WO 0226884 | 12/1986 |
| WO | WO 99/07342 | 2/1999 |

OTHER PUBLICATIONS

International Journal of Pharmaceutics 62 (1990) R9–R11: The effect of tablet size on the gastric emptying of non–disintegrating tablets by R. Khosla and S.S. Davis.
Pharmaceutical Research, vol. 8, No. 10, (1991) 1281–1285: Correlation of the Gastric Emptying of Nondisintegrating Tablets with Gastrointestinal Motility by Alastair J. Coupe et al.
Journal of Controlled Release 26 (1993) 39–47: Multi–layered hydrophillic matrices as constant release devices by U. Conte et al.
International Journal of Pharmaceutics 38 (1987) 221–225: The influence of food on the absorption of acyclovir: . . . by Clive G. Wilson et al.
Journal of Controlled Release 19(1992) 131–134: In vitro and in vivo studies of enzyme–digestible hydrogels for oral drug delivery by Waleed S.W. Shalaby et al.
British Journal of Clinical Pharma. vol. 21 (1986) 459–462: Human gastrointestinal absorption of acyclovir from tablet duodenal infusion and sipped solution by L.D. Lewis et al.
Journal of Pharmaceutical Sciences 82(8)1993: The cutoff size for gastric emptying of dosage forms.

* cited by examiner

*Primary Examiner*—Thurman K. Page
*Assistant Examiner*—Frank Choi

(57) ABSTRACT

The present invention is directed to a multilayered dosage form which is adapted for retention in the stomach and useful for the prolonged delivery of an active agent to a fluid environment of use. The active agent dosage form is a multilayer core, often bilayer, formed of polymer matrices that swell upon contact with the fluids of the stomach. At least one layer of the multilayered dosage form includes an active agent. A portion of the polymer matrices are surrounded by a band of insoluble material that prevents the covered portion of the polymer matrices from swelling and provides a segment of the dosage form that is of sufficient rigidity to withstand the contractions of the stomach and delay expulsion of the dosage form from the stomach until substantially all of the active agent has been dispensed.

26 Claims, 6 Drawing Sheets

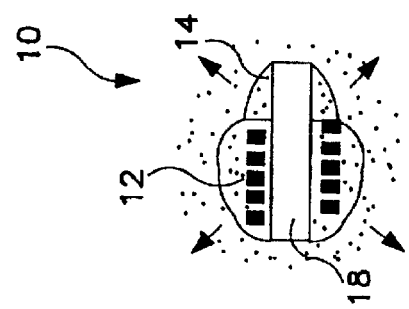
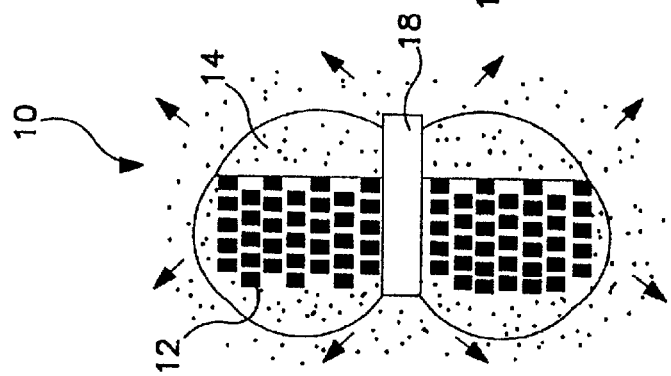
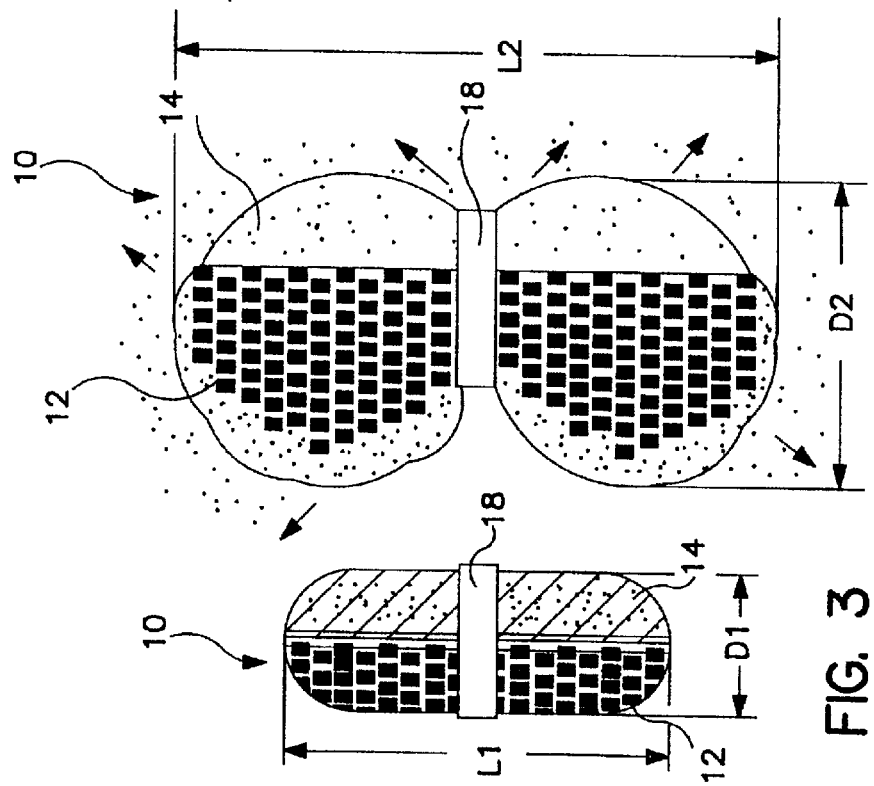
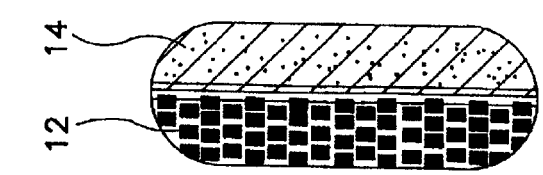
FIG. 2  FIG. 3  FIG. 4  FIG. 5  FIG. 6

GASTRIC RETENTION DOSAGE FORM HAVING MULTIPLE LAYERS

This application claims the priority of provisional application No. 60/113,560, filed Dec. 23, 1998.

FIELD OF THE INVENTION

The present invention is related to the prolonged release of an active agent from a dosage form. More particularly, it relates to a multilayered active agent dosage form having a highly swellable layer and a drug layer, the dosage form being adapted for retention in the stomach for a prolonged period.

BACKGROUND OF THE INVENTION

Controlled release dosage forms that provide for prolonged delivery of active agent formulations to the environment of use have found application for increasing numbers of active agents. However, with respect to pharmaceutical and veterinary active agent formulations, there has been a need not only to provide for prolonged delivery of the active agent over time, but also to provide prolonged delivery of the active agent at a particular location or locations in the environment of use, such as in the stomach.

Certain active agents are absorbed primarily from the small intestine. Generally, the time of passage of different particles through the small intestine does not vary significantly, and passage is generally independent of food intake and particle size. Thus, active agent dissolved in liquid, solid active agent dispersed in liquid and relatively larger delivery units of active agent, such as microcapsules and the like, will traverse the length of the small intestine in substantially the same time frame, usually about 3–5 hours. For active agents that are not easily absorbed by the small intestine or that do not dissolve readily, the window for active agent absorption in the small intestine may be too short to provide a desired therapeutic effect. This fact often creates a need for frequent dosing of active agent in order to provide and maintain adequate levels of active agent in blood plasma. The need for frequent dosing presents compliance problems and is often inconvenient for the user as well.

Since it has been found difficult to alter the transit time of active agent through the small intestine, some emphasis has been placed on attempting to control the transit time of active agents in the stomach. Most active agents are not well absorbed in the stomach, but even in those instances where the active agent is not well absorbed, the continuous release of active agent in the stomach over a prolonged time period will dispense active agent over that same period of time to the small intestine where it can be absorbed.

The physiological behavior of the stomach is usually determined by whether it contains food or is empty. Food is mixed and partially digested in the distal stomach (antrum). As the stomach undergoes contractions, partially digested material is discharged into the small intestine and non-digested material is retropelled into the main part of the stomach for further digestion. In the fed state, non-digested material is not generally able to leave the stomach. At the end of a digestive period, the stomach enters the fasting stage and begins a cycle called the interdigestive myoelectric motor cycle or IMMC.

The IMMC can be considered to be divided into four phases: (1) phase 1 is an approximately one hour period with no contractions; (2) phase 2 is about a forty minute period of intermittent potentials and contractions that increase in intensity over time; (3) phase 3 is a relatively short period, generally between about five to fifteen minutes, of intense contractions (commonly called the "housekeeper wave") that completely empties the stomach; and (4) phase 4 is a short transitory period between the intense activity of phase 3 and the quiescence of phase 1. The different phases move distally from the stomach to the terminal ileum over an approximately two hour period as the cycle is repeated. Since the cycle is interrupted by the receipt of food by the stomach, it is possible to delay the emptying phase, phase 3, by maintaining a fed state. However, it is not practical to regularly maintain the fed state over a long period of time. Consequently, a need exists for a delivery device that can remain in the stomach for a significant period, whether in the fed or fasted state, and deliver active agent to the stomach over a prolonged period of time.

A variety of studies have been conducted in dog and in man to determine sizes of objects that would be retained in the stomach during the fed stage and also in the fasting stage when IMMC is present. Khosla and Davis, *International Journal of Pharmaceutics*, Vol. 62 (1990), pages R9–R11 have reported that a particle size less that 2 mm generally results in emptying from the stomach of the dog. Non-disintegrating tablets having sizes of 7, 11 and 13 mm in diameter were emptied from the human stomach, but the larger sized tablets tended to remain in the stomach longer than the small sized tablets. Tablets larger than 11 mm tended to be emptied only during the IMMC. Davis et al., *Pharmaceutical Research*, Vol. 8, No. 10 (1991) has described retention of radio-telemetry capsules having a size of 25×8 mm in the stomach of human subjects past phase 3 of the IMMC. Timmermans et al., *Journal of Pharmaceutical Sciences*, Vol. 82, No. 8 (1993) has reported the mean resting pyloric diameter in humans as 12.8±7.0 mm. Accordingly, it is important that gastric retentive delivery vehicles are adapted to disintegrate, dissolve or erode to sizes that permit eventual elimination of the vehicle without causing gastric obstruction.

Various attempts to provide active agent delivery devices that remain in the stomach for extended periods or time have been described previously. For example, U.S. Pat. No. 4,851,232 describes a hydrogel reservoir containing tiny pills having a active agent core surrounded by a wall controlling delivery of active agent to the stomach. The hydrogel swells in the stomach to facilitate retention of the active agent reservoir in the stomach over time.

U.S. Pat. No. 4,871,548 describes a dosage form including a mixture of low and high number average molecular weight hydroxypropylmethylcellulose polymers and active agent that swells when in the stomach.

U.S. Pat. No. 4,767,627 describes substantially planar devices formed of bioerodible polymer including active agent that may be compressed and folded for oral administration and then released and unfolded in the stomach, where the devices are to be retained over an extended period of time. The devices have a longest diameter of between 1.6 and 5 cm. It is suggested that as an alternative to incorporating the active agent into the device a controlled release active agent module, mechanically or osmotically driven, can be glued or tethered to the device.

U.S. Pat. No. 5,443,843 describes a plurality of compressible retention arms and an attached controlled release device which in the expanded form resists gastrointestinal transit. The system can have a collar or a belt for receiving and holding a active agent-containing, orally-administrable controlled release device. In a fully expanded configuration for human use, the system is described as having minimum and maximum dimensions of 2.5 and 6.0 centimeters, respectively.

U.S. Pat. No. 5,007,790 describes a sustained release active agent dosage form in the form of a capsule or tablet that includes a plurality of hydrophilic water-swellable, cross-linked polymer particles that swell in the stomach to promote gastric retention and permit gastric fluid to penetrate the particles to dissolve active agent and deliver it to the stomach in the solution state. The particles are indicated to retain their physical integrity over the dosing period. Initially sized particles, indicated to be preferably spherical, are disclosed to be in the range of 50 μm to 2 mm, swell to a size of about 3 mm. A plurality of particles are packed into a capsule for administration to a patient.

U.S. Pat. No. 5,582,837 describes a dosage form similar to that of U.S. Pat. No. 5,007,790, without the use of a cross-linked hydrophilic polymer. The particles are described as slippery and soft, preferably spherical, and having dimensions on the order of 6 to 18 mm in the swollen state. The particles can be packed into capsules containing 7–25 spherical particles, depending on the size, or formulated into tablets that contain from 2–25 spherical particles.

The use of albumin-cross-linked polyvinylpyrrolidone hydrogels to deliver flavin mononucleotide to dogs has been described by Park et al. in *Journal of Controlled Release*, Vol.19 (1992) pages 131–134. The hydrogels were maintained in the stomachs of dogs for extended periods, even in the fasted state. Gels with a glassy core tended to remain in the stomach longer than hydrogels without the glassy core. Control of the size of the core was attempted by administration of water in the stomach. While it is possible to control the dimensions of the hydrogel in the dry state, controlling the size of the glassy core within the hydrogel after administration to a subject by addition of water is not suitable for fabrication of a dosage form that can routinely and controllably be retained in the stomach of a subject over a prolonged period of time.

While it is important that the delivery device be adapted to remain in the stomach for a prolonged period, it is also important that the device deliver active agent in a controlled manner. Even though control over the delivery of active agents that are released from a highly swellable matrix as described in International Application WO 99/07342, published Feb. 18, 1999, may be achieved in many instances, a greater degree of control is possible when the retention function of the dosage form and the drug delivery function of the dosage form are addressed individually.

Delivery systems, such as those described below, are representative of the many different systems have been suggested for controlled delivery of active agents from a dosage form over a prolonged period of time with no particular emphasis on retention of the dosage form in the stomach for a prolonged period.

For example, U.S. Pat. No. 4,290,426 to Lusted et al describes a cylindrical dispenser for releasing a beneficial agent into a fluid environment at a rate that is governed by the fluid induced relaxation of a polymeric agent contained within the dispenser. The cylindrical dispenser includes an impermeable container that has within it a reservoir and a passageway from the reservoir to the exterior of the container. The reservoir contains a polymer and a beneficial agent. The polymer imbibes fluid from the environment and thereby undergoes relaxation, releasing the beneficial agent from the device. The amount of agent released is dependent on the rate of relaxation of the polymer over time.

Coated dosage forms have also been suggested for delivery of a controlled amount of a beneficial agent over a prolonged period of time. U.S. Pat. No. 5,256,440 describes a process for producing a film coated dosage form. A continuous groove is inscribed in a dosage form core. A latex film is coated onto the core, the groove defining a fixed zone and a detachable zone for the film. The detachable portion of the latex film detaches when it is exposed to the environment of use, thereby exposing a discrete portion of the dosage form core surface. The remainder of the film remains attached to the dosage form core. The exposed portion of the dosage form surface erodes and releases active agent to the environment of use.

Coated tablets for constant and prolonged active agent release are described by Conte et al in *J. Controlled Release*, Vol. 26, (1993) pages 39–47. These GEOMATRIX™ Systems are swellable matrices that are coated or tableted with polymeric barrier layers. Release performances of the systems are modulated as a result of the reduction of the releasing surface exposed to the dissolution medium by the polymeric barrier layer coatings. As the extent of coating of the system's surface is increased, the release kinetics of the system shift toward constant release. These systems are further described in U.S. Pat. No. 4,839,177 to Colombo et al.

U.S. Pat. No. 5,780,057 describes a two or three layered tablet where at least one of the layers swells by contact with biological fluids to promote retention of the tablet in the stomach where the active ingredient may be slowly released. The description indicates that at least one of the layers acts as a barrier for a predetermined period of time to the active agent that is contained one of the other layers.

U.S. Pat. No. 5,534,263, which is incorporated herein by reference, describes a dosage form useful for the prolonged delivery of an active agent formulation in the form of a matrix having two or more insoluble bands on the surface of the matrix. The exposed surfaces of the matrix erode in a manner that creates additional surface areas to provide for prolonged release of an active agent formulation with determined release profiles. That patent is not concerned with dosage forms that are retained in the stomach for a prolonged period of time.

Additional oral, controlled-release dosage forms include elementary osmotic pumps, such as those described in U.S. Pat. No. 3,845,770, mini-osmotic pumps such as those described in U.S. Pat. Nos. 3,995,631, 4,034,756 and 4,111,202, and multi-chamber osmotic systems referred to as push-pull, push-melt and push-stick osmotic pumps, such as those described in U.S. Pat. Nos. 4,320,759, 4,327,725, 4,449,983, 4,765,989, 4,892,778, 4,940,465, 4,915,949 and 5,126,142, all of which are incorporated herein by reference.

Administration of acyclovir by sipped solution over a four-hour period has been described in *Br. J. clin. Pharmac.*, 21, 459–462 (1986) to achieve an increased contact time with the human stomach and the gastrointestinal tract. The total amount of acyclovir absorbed was increased over that observed with administration of acyclovir tablets. However, continuous oral administration requiring the interaction of the patient is not what would generally be considered suitable therapy. The influence of food on gastric retention time and the absorption of acyclovir has been reported in *International Journal of Pharmaceutics*, Vol. 38 (1987), pages 221–225. As reported there, compared to a lighter meal, the heavier meal slowed the rate of gastric emptying, prolonged small intestinal transit time and decreased absorption of the active agent.

SUMMARY OF THE INVENTION

As can be observed in the above-referenced patents and publications, devices have been described that provide for prolonged delivery of an active agent and retention in the gastric environment. However, there remains a continuing need for improved systems for delivering an active agent to the gastric environment over a prolonged period of time and in a reliable, controllable and reproducible manner.

In one aspect, the invention comprises an active agent dosage form adapted for gastric retention comprising (a) a first layer comprising a swellable, water-soluble polymer, (b) a second layer comprising a therapeutically-effective amount of an active agent, the second layer being laminated with the first layer at a common surface, and (c) at least one band of insoluble material circumscribing and binding together the first layer and the second layer, the first layer being adapted to swell in the stomach to facilitate retention of the dosage form in the stomach over a prolonged period of time. Preferably, the release of the active agent from the second layer is independent of the composition of the first layer and occurs over a prolonged period of time. Examples of water soluble polymers include polyethylene oxide, hydroxypropyl cellulose, hydroxypropyl methyl cellulose, hydroxyethyl cellulose, sodium carboxy methylcellulose, calcium carboxymethyl cellulose, methyl cellulose, polyacrylic acid, maltodextrin, pre-gelatinized starch, guar gum, sodium alginate, or polyvinyl alcohol, and most preferably high molecular weight polyethylene oxide, e.g., Polyox® brand of polyethylene oxide (Union Carbide Corporation, Danbury, Conn.). The first layer preferably swells more rapidly and to a greater extent than does the second layer. The first layer may be gel-like and exhibit a slippery external surface.

In another aspect, the first or second layers of the above-described dosage form comprises a hydroattractant selected from low-substituted hydroxypropyl cellulose, microcrystalline cellulose, cross-linked sodium or calcium carboxymethyl cellulose, cellulose fiber, cross-linked polyvinyl pyrrolidone, cross-linked polyacrylic acid, cross-linked Amberlite resin, alginates, colloidal magnesium-aluminum silicate, corn starch granules, rice starch granules, potato starch granules, pregelatinized starch, sodium starch glycolates, guar gum, soybean fiber, psyllium husk fiber, rice husk fiber, wheat fiber, alginic acid derivatives such as sodium alginate and alginic acid, silicates such as bentonite, colloidal magnesium and aluminum silicate (Veegum), gelatin, cross-linked gelatin, sodium carboxymethyl starch, sugars and sodium chloride.

In another aspect, the invention comprises the dosage form as described above wherein the weight percent of the water soluble polymer in the first layer is about 5 to 100 weight percent and weight percent of the hydroattractant in the first layer is about 0 to 60 weight percent, and the weight percent of the water soluble polymer in the second layer is about 5 to 95 weight percent and the weight percent of the hydroattractant is about 5 to 70 weight percent. The dosage form of the invention releases the active agent over a prolonged period time of at least about 3 hours, more often between 8 to 12 hours.

In still another aspect, the second layer may be formed of a plurality of sublayers, each containing differing amounts of active agent or different active agent or each being of different thickness to provide active agent release profiles that vary with time.

In a further aspect, the invention comprises a method of treating a subject in need thereof with an active agent that comprises administering to the subject a multilayered dosage form adapted to be retained in the stomach over a prolonged period of time, the dosage form comprising a first layer adapted to swell in the stomach of the subject and retain the dosage form in the stomach for a prolonged period of time, and a second layer adapted to deliver to the subject an active agent at a variable rate of delivery. The second layer may be comprised of multiple laminates, each having a different active agent concentration per unit volume and/or different thickness. The method may comprise administering one or more dosage forms to the subject in the fed state at the start of each dosing period, such as within one hour of the subject consuming food.

BRIEF DESCRIPTION OF THE DRAWINGS

The figures are not drawn to scale, but are set forth to illustrate various embodiments of the invention. Like numbers refer to like structures.

FIG. 2 is a schematic of bilayer core of the dosage form prior to completion of fabrication of the dosage form;

FIG. 3 is a completed dosage form of the invention;

FIG. 4 illustrates the dosage form of the invention soon after administration where the retention layer of the dosage form and the drug layer have swelled to substantially maximum dimensions;

FIG. 5 illustrates the dosage form of the invention at an intermediate time after administration where the retention layer and the drug layer have eroded or dissolved in the stomach environment, but at a stage where the retention layer is still large enough to effectively maintain the dosage form in the stomach;

FIG. 6 illustrates the dosage form at a later time than illustrated in FIG. 5, when the retention layer has eroded or dissolved to an extent that the dosage form may be expelled from the stomach through the pylorous;

DETAILED DESCRIPTION OF THE INVENTION

Figure 1:
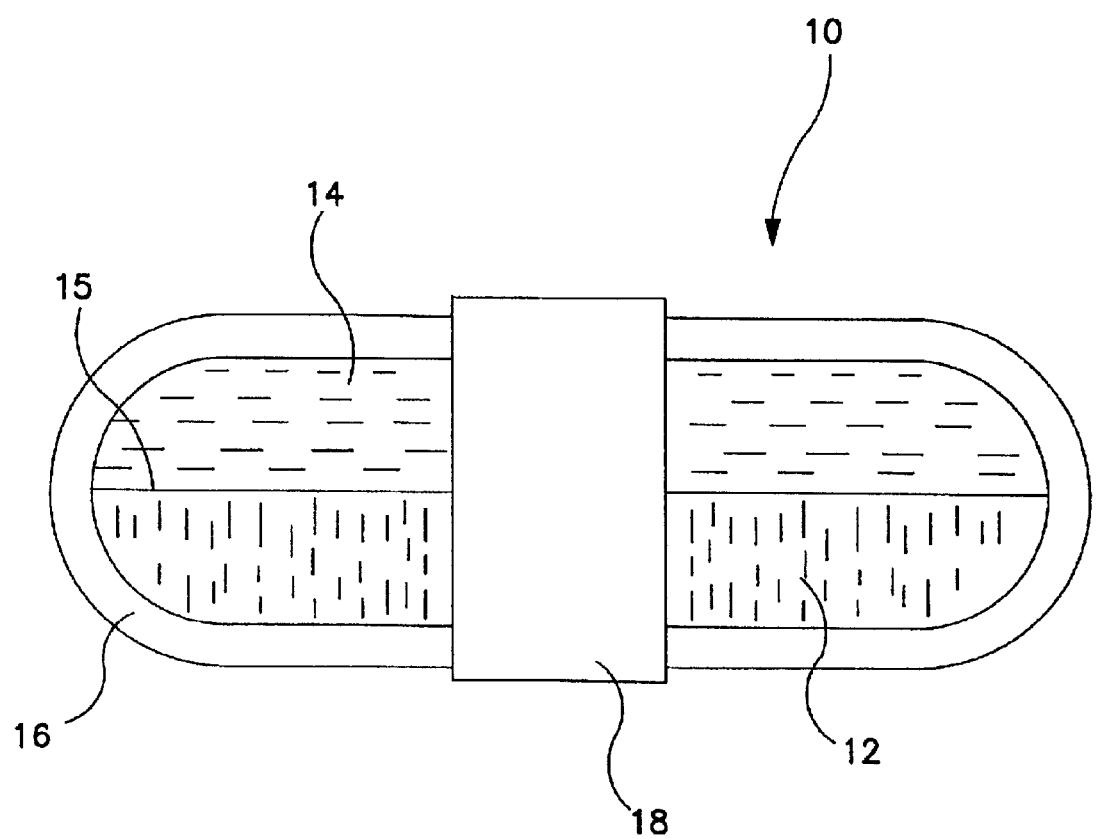
FIG. 1 is a schematic illustrating a dosage form of the present invention.

The present invention provides an active agent dosage form that is retained in the stomach for a sustained period of time and that is useful for the delivery of an active agent formulation to a fluid environment of use over a prolonged period of time. In International Application WO 99/07342, published Feb. 18, 1999, one manner of providing such a dosage form is disclosed. However, the particular active agent dosage form described therein is not always suitable for all applications. It was discovered that there are competing considerations when attempting to retain a dosage form in the stomach of a subject for a prolonged period of time and at the same time reliably deliver the active agent over that period.

Two such competing considerations are the requirement to have the dosage form small enough for easy swallowing and yet have the dosage form swell and become large enough after administration to insure retention in the stomach for a prolonged period of time. A second set of competing aspects is the need to incorporate enough active agent into the dosage form so that it can be available for release over the prolonged period of time while not detrimentally affecting the ability of the dosage form to swell and increase in size so as to be retained in the stomach for the requisite period of time. Another consideration is to be able to control the rate of release of the active agent from the dosage form without compromising the rate at which the swollen polymer matrix is eroded or dissolved in the stomach and consequently reduce the retention time below acceptable levels.

Accordingly, it has been surprisingly discovered that the dosage form of this invention may be fabricated with an individual portion that does not contain active agent and an individual portion that does contain active agent, those two portions being laminated together and further joined by an insoluble band that maintains the separate portions together during the prolonged period in which the dosage form is retained in the stomach; that the dosage form may be loaded with large amounts of active agent when the clinical application requires; that the dosage form will be retained in the stomach over a prolonged period; and that the dosage form will be effective with separate portions having different swelling, erosion and dissolution characteristics. The particular improvements and characteristics comprising the invention are described below.

Definitions

The phrase "prolonged period" or "prolonged period of time" intends a time period that lasts for several hours to about 24 hours, usually up to about 12 hours, and often between about 3 and 14 hours, and most often at least 6 hours.

The phrase "prolonged delivery" intends a duration of delivery extending over a time period that lasts for several hours to about 24 hours, usually up to about 12 hours, and often between about 3 and 14 hours, and most often at least 6 hours.

By "insoluble" is intended a material that will not substantially dissolve in the environment of use during the delivery period.

The term "active agent" refers to an agent, drug, compound or other substance, or compositions and mixtures thereof, that provide some pharmacologic, often beneficial, effect. Reference to a specific active agent shall include where appropriate the active agent and its pharmaceutically acceptable salts.

The term "polymer matrix" as used herein means a water soluble, high molecular weight polymer and, optionally, a hydroattractant in admixture therewith.

The term "active agent formulation" intends the active agent or the active agent optionally in combination with pharmaceutically acceptable carriers and additional inert ingredients.

The terms "adapted for gastric retention" or "gastric retentive" mean, with respect to the dosage form of this invention, that the dosage form will remain in the stomach of a subject for a prolonged period of time.

The terms "rigid" and "semi-rigid" mean, with respect to a portion of the polymer matrix as defined above, that such portion will not swell and form a gel when initially contacted with gastric fluid.

The term "bioerodible" intends a material that will, at least in part, dissolve, degrade or erode in the fluid environment of use.

The term "bioequivalent" intends, with respect to an active agent dosage form of this invention, that there is greater than a 90% probability that the bioavailability of the active agent as determined by standard methods is 80–125% of the defined dosage form and that there is greater than a 90% probability that the maximum blood plasma concentration and the minimum blood plasma concentration of the active agent as measured by standard methods is 80–125% of the defined dosage form.

The term "polymer" means a material formed from a single polymer or a mixture of polymers.

The term "swellable" means, with respect to a polymer or a polymer matrix, that the polymer or polymer matrix is capable of imbibing fluid and expanding when in contact with fluid present in the environment of use.

The terms "therapeutically effective" amount or rate refer to the amount or rate of the active agent needed to effect the desired pharmacologic, often beneficial, result.

The invention will be better understood with reference to the drawings and the description herein.

FIG. 1 depicts one embodiment of the delivery device 10 according to the present invention. The delivery device or active agent dosage form 10 comprises a first layer 12 of material that swells upon imbibing fluid and a second layer 14, laminated at a common surface 15. The first layer 12 conveniently is formed of a highly swellable polymer which will initially swell upon imbibing fluid and subsequently dissolve or erode after administration in the stomach of a subject over a prolonged period of time. Second layer 14 comprises a therapeutic agent, most often dispersed or dissolved in a carrier. Second layer 14 may be formed of material that swells to some extent in the stomach and which also will dissolve or erode in the environment of use, i.e., primarily in the stomach of the subject to whom the dosage form has been administered. In most instances, the material forming first layer 12 will swell to a greater extent than that the material forming second layer 14. A band 18 circumscribes the two layers 12 and 14 and maintains the two layers together during operation. This is particularly important since the different swelling characteristics of layers 12 and 14 may create a tendency toward delamination and separation at the common surface 15. Band 18 typically is insoluble and provides a certain degree of rigidity near the central portion of the dosage form because of the inability of the first and second layers to swell to any appreciable extent in the area under the band. Optionally, a soluble coating 16 may be applied to the two layers prior to the banding process to provide a smooth surface that facilitates swallowing of the dosage form. Also, an optional second, soluble coating (not shown) may be applied over the completed dosage form to provide a continuously smooth external surface.

Representative examples of the swellable polymer comprising high molecular weight, water-soluble polymers useful for the fabrication of first layer 12 are polyethylene oxide and cellulosic polymer derivatives including hydroxypropyl cellulose, hydroxypropyl methyl cellulose, hydroxyethyl cellulose, sodium carboxy methylcellulose, calcium carboxymethyl cellulose, methyl cellulose, as well as noncellulosics such as maltodextrin, polyvinyls, polyvinyl alcohol, polyacrylic acids, alginates, gelatin, natural gums, including guar, lightly crosslinked versions of these polymers, starches, starch graft copolymers and the like. The polymers generally have number average molecular weights over 50,000 grams per mole, such as between 50,000 and 10,000,000 grams per mole and representative viscosities, e.g. for polyethylene oxide in the range of 12–20,000 cps (5% aq, 25° C., MW 100,000–900,000), 400–4000 cps (2% aq, 25° C., MW 1,000,000–2,000,000) and 1500–15,000 cps (1% aq, 25° C., MW 4,000,000–8,000,000) [Brookfield viscometer, rotational spindle]; for methylcellulose in the range of 1,500–18,000 cps (2% aq, 20° C., MW 62,000–134,000) [Ubbelohde tube viscometer]; for hydroxypropyl methylcellulose in the range of 4,000–100,000 cps (2% aq, 20° C., MW 88,000–242,000) [Ubbelohde tube viscometer]; for hydroxyethyl cellulose in the range of 75–400 cps (5% aq, 25° C., MW 90,000–200,000), 400–6500 cps (2% aq, 25° C., MW 300,000–720,000) and 1500–5,000 cps (1% aq, 25° C., MW 1,000,000–1,300,000) [Brookfield viscometer, rotational spindle]; for guar about 5100 cps (1%) [Brookfield viscometer, rotational spindle]; for poly(methyl vinyl ether/maleic anhydride) in the range of 15 to greater than 200 cps (5% aq., MW 20,000–80,000) [Brookfield viscometer, rotational spindle]; for polyvinyl alcohol in the range 27–65 cps (4%aq, 20° C. [Hoeppler falling ball method and 1100–1500 cps (10%aq, 25° C.) [Brookfield viscometer, rotational spindle; for sodium carboxymethyl cellulose in the range of 25–50 cps (2% aq, 25° C.) (MW 90,000) to about 2,500–6,000 cps (1% aq, 25° C.) (MW 700,000) [Brookfield viscometer, rotational spindle]; and for sodium polyacrylic acid 5000–80,000 (0.5% aq) (MW 750,000–4,000,000,000) [Brookfield viscometer, rotational spindle]. Polymers having molecular weights between 300,000 and 8,000 000 grams per mole are preferred, and those having molecular weights between about 2,000,000 to 8,000,000 grams per mole are especially preferred. Polyethylene oxide having a number average molecular weight between about 5,000,000 to 8,000,000 grams per mole is most especially preferred, e.g. Polyox 303 and Polyox 308. Also, especially preferred are methylcellulose type/grade A15C, A4M, A18 M and hydroxypropyl methylcellulose type/grade K4M, K15M, K100M, E4M and F4M (Dow Chemical Company); hydroxyethyl cellulose such as Natrosole HEC; hydroxypropyl cellulose such as Klucel (Grades H, M, G, J, L, E—Aqualon Company); guar such as Supercol® Guar U (Aqualon Company); pectin such as GENU Pectin (Aqualon Company); carrageenan such as GENU Carrageenan (Aqualon Company); poly(methyl vinyl ether/maleic anhydride) such as Gantrez® AN Copolymer (AN-119, -139, -149, -169, -179, GAF Corporation); polyvinyl alcohol such as Elvanol® 71-30, Elvanol® 85-80, Elvanol® 55-65, Elvanol® 50-42 and Elvanol® HV (DuPont); sodium carboxymethyl cellulose such as Aqualon cellulose gum grade 7H4; polyacrylic acids such as Carpobol® resin grades 934P, 940, 941, 971P, 974P, 980, 981, 1382, 2984, 5984, ETD 2001, ETD 2050, calcium polyacrylic acids such as Noveon® resin grades AA-1, CA-1 and CA-2, and sodium polyacrylic acid (BF Goodrich, Cleveland, Ohio).

Polymers that impart a surface lubricity to first layer 12 are especially preferred, and may be exemplified by polyethylene oxides sold under the trademark Polyox, e.g. Polyox 303 and Polyox 308. The combination of surface lubricity, the gel-like nature of the swollen polymer, the rigid section of the dosage form provided by band 18 and the resulting non-swollen section of the dosage form, and the particular size parameters of the swollen dosage form all appear to contribute to the characteristic of the dosage form to be retained in the stomach for a prolonged period of time.

First layer 12 may be formed with a hydroattractant mixed with the water soluble polymer. Representative hydroattractants, that may be used are described below with regard to the second layer 14. The use of a hydroattractant generally facilitates rapid swelling of first layer 12 in the stomach and generally provides a greater assurance that the dosage form will attain a swollen size after administration that resists expulsion through the pylorus. Fiberlike hydroattractants additionally serve to impart a fiber reinforced gel structure.

Second layer 14 may also conveniently be formed of a polymer base that swells to some extent to allow for erosion and dissolution in the environment of use to facilitate release of the active agent in a controlled fashion. Polymers of the classes described for first layer 12 may be utilized. However, generally polymer materials that do not swell to the same extent as those employed in first layer 12 will be utilized. More limited swelling allows for increased quantities of active agent to be loaded into the second layer 14 than would otherwise be possible. Preferred materials include the water soluble polymers such as described above, particularly the polyethylene oxides having molecular weights of between about 100,000 to 900,000 are preferred.

The second layer 14 may also preferentially include a hydroattractant to draw in water from the environment of use to facilitate release of active agent when the active agent is present initially in a dry state. When active agent is provided in a liquid, active agent formulation, as will be described later, the use of a hydroattractant may be optional, since the carrier in which the particles containing the liquid, active agent formulation typically will dissolve or erode to allow the particles to be released to the environment of use, and subsequently release active agent at the absorption site.

Representative examples of hydroattractants are water-insoluble polymers such as low substituted hydroxypropyl cellulose, microcrystalline cellulose (Avicel), cross-linked sodium or calcium carboxymethyl cellulose, cellulose fiber (Solka-Floc, Arbocel or Elcema), cross-linked polyvinyl pyrrolidone (Polyplasdone XL), cross-linked Amberlite resin, alginates (Satialgine), colloidal magnesium-aluminum silicate (Veegum), corn starch. granules, rice starch granules, potato starch granules, wheat starch granules, sodium carboxymethyl starch (Expotab, Primojel), corn starchlacrylamidelsodium acrylate copolymer, acrylamide/sodium acrylate copolymer and the like. A particularly suitable hydroattractant is hydroxypropyl cellulose having a hydroxypropyl content of between about 8–15 weight percent, and preferably about 10–13 weight percent, such as that supplied as Low Substituted Hydroxypropyl Cellulose grade 11 as manufactured by Shin-Etsu Chemical Company, Ltd., Tokyo, Japan. Optionally, non-polymeric water-soluble hydroattractants can be incorporated into layer 12. These include sodium chloride, sugars such as sorbitol, mannitol, glucose, maltose, sucrose, lactose, acids such as citric acid, tartaric acid, succinic acid, gas-generating agents such as sodiium or potassium bicarbonate which react with gastric fluids to produce carbon dioxide gas, and the like.

As noted earlier, optionally, hydroattractants, such as those described above, may be included in the first layer 12 as well. Hydroxypropyl cellulose having a hydroxypropyl content of between 8–15 weight percent is preferred, and most preferred are those having a hydroxypropyl content of about 10–13 weight percent, such as Low Substituted Hydroxypropyl Cellulose grade 11 exemplified above.

Typically, the water soluble, high molecular weight polymer in the polymer matrix of the first layer 12 is present in from about 5% to about 100% by weight based on the total weight of layer 12. Typically, the water soluble polymer forming layer 14 is present in from about 5% to about 90% of the active agent formulation layer 14, and the hydroattractant is present in from about 5% to about 70% by weight based on the total weight of the active agent formulation layer 14. The particular percentages will be chosen to provide the desired retention time in the stomach and the desired release profile of active agent. However, it is presently preferred to have the polymer matrix forming layer 12 contain about 50% of a highly swellable, water soluble polymer, 25% of cellulose fiber and 25% sodium chloride, and the polymer matrix forming second layer 14 contain from about 10 weight percent to about 50 weight percent of the water soluble, high molecular weight polymer and from about 10 weight percent to about 60 weight percent of the hydroattractant. Weight percentages of water soluble, high molecular weight polymer in the range of 10 to 40 weight percent and hydroattractant in the range of 25 to 35 in second layer 14 are especially preferred, the remaining percentage being active agent or an active agent composition.

Dosage form 10 is conveniently cylindrically shaped with rounded ends that facilitate administration of the dosage form in its non-swollen state. In FIG. 2, the device 10 is shown in preparation, without the addition of an overcoat, prior to application of the insoluble material or band 18 shown in FIG. 3. The insoluble material exemplified as band 18, circumscribes a portion of the outer surface of the dosage form 10, including both layer 12 and layer 14. While a single band is illustrated in FIG. 3, additional bands can be utilized depending on the particular application for which the device is being used. For ease of illustration, optional coating 16 and any optional overcoat have been omitted in FIGS. 2–6.

The band of insoluble material 18 is applied to the outer surface of the layers 12 and 14. The insoluble material imparts rigidity particularly to the gel-forming polymer matrix forming layer 12 to manage gastric retention time and further control the delivery profile of the active agent of interest from layer 14. Band 18 typically exhibits low water permeability and will prevent that portion of the polymer matrices which it surrounds from imbibing fluid, thus substantially limiting any swelling of the polymer matrix of layers 12 and 14 at that location. In addition, given that the layers 12 and 14 often may be formed of different materials having rates of swelling that tend to delaminate the dosage form at the common surface 15, band 18 also serves to retain the two layers together and maintain the integrity of the dosage form 10 during most of its lifetime. The number, size, and placement of the insoluble bands that are applied may be varied to adjust the active agent delivery profile and the retention time in the stomach. For example, bands 0.1 mm to about 12 mm in width, preferably between about 0.5 and 8 mm, may be applied onto the active agent formulation matrix surface. Further, between about 1 and 10 bands may be used, but generally between about 1 and 3 are affixed to the bilayer core. The bands may be placed close together (i.e., within about 0.5 mm of each other) or may be placed about 8 to 12 mm apart.

FIG. 4 illustrates dosage form 10 in its initial configuration after it has imbibed fluid and swelled in those areas not surrounded by band 18. Because of the low fluid imperme-ability of band 18, the portion of dosage form 10 surrounded by band 18 does not appreciably imbibe fluid and the polymer in such portion of the dosage form does not swell to any significant extent. FIG. 5 illustrates a sequential state of dosage form 10 after it has begun to be eroded by or dissolve in the gastric fluid. FIG. 6 illustrates the dosage form after it has been substantially eroded by gastric fluid and contractions of the stomach. Eventually, dosage form 10 will be reduced to such a size as to enable it to be expelled from the stomach.

The insoluble material comprising band(s) 18 may be any material that is nontoxic, biologically inert, nonallergenic and nonirritating to body tissue, that exhibits little impermeability to liquids, and that maintains its physical and chemical integrity in the environment of use for at least a portion of the dispensing period. The bands may be formulated with neutral charge polymers which are insoluble in gastric fluid or may be formulated with anionic polymers which are insoluble in gastric fluid and dissolve in intestinal fluid. The low liquid permeability of the insoluble material serves to limit swelling of the polymer matrix in that section of the polymer matrix that is surrounded by the band.

Insoluble materials from which the bands may be prepared include, for example, polyethylene, polystyrene, ethylene-vinyl acetate copolymers, polycaprolactone and Hytrel® polyester elastomers (Du Pont). Additional banding materials include but are not limited to polysaccharides, cellulosics, cellulose acetate, cellulose acetate propionate, cellulose acetate phthalate, cellulose acetate butyrate, cellulose acetate pseudolatex (such as described in U.S. Pat. Nos. 4,931,285 and 5,024,842), ethyl cellulose, ethyl cellulose. pseudolatex (such as Surelease® as supplied by Colorcon, West Point, Pa. or Aquacoat™ as supplied by FMC Corporation, Philadelphia, Pa.), nitrocellulose, polylactic acid, poly-glycolic acid, polylactide glycolide copolymers, polycaprolactone, polyvinyl alcohol, polyvinyl acetate, polyethylene vinylacetate, polyethylene teraphthalate, polybutadiene styrene, polyisobutylene, polyisobutylene isoprene copolymer, polyvinyl chloride, polyvinylidene chloride-vinyl chloride copolymer, copolymers of acrylic acid and methacrylic acid esters, methacrylic acid copolymers, copolymers of methylmethacrylate and ethylacrylate, ammoniomethacrylate copolymer, latex of acrylate esters (such as Eudragit® supplied by R öhmPharma, Weiterstadt, Germany), polypropylene, copolymers of propylene oxide and ethylene oxide, propylene oxide ethylene oxide block copolymers, ethylenevinyl alcohol copolymer, poly sulfone, ethylene vinylalcohol copolymer, polyxylylenes, polyamides, rubbers, such as styrenebutadiene, polyisobutylene and the like, natural and synthetic waxes, paraffin, camauba wax, petroleum wax, white or yellow bees wax, castor wax, candelilla wax, rice bran wax, microcrystalline wax, stearyl alcohol, cetyl alcohol, bleached shellac, esterified shellac, chitin, chitosan, silicas, polyalkoxysilanes, polydimethyl siloxane, polyethylene glycol-silicone elastomers, crosslinked gelatin, zein, electromagnetic irradiation crosslinked acrylics, silicones, or polyesters, thermally crosslinked acrylics, silicones, or polyesters, butadiene-styrene rubber, glycerol ester of partially dimerized rosin, glycerol ester of partially hydrogenated wood rosin, glycerol ester of tall oil rosin, glycerol ester of wood rosin, pentaerythritol ester of partially hydrogenated wood rosin, pentaerythritol ester of wood rosin, natural or synthetic terpene resin and blends of the above.

The banding materials often are also formulated with plasticizers, and optionally with wetting agents, surfactants, opacifiers, colorants, flavorants, taste-masking agents, and the like. Examples of typical plasticizers are as follows: polyhydric alcohols, polyethylene glycol, glycerol, propylene glycol, acetate esters, glycerol triacetate, triethyl citrate, acetyl triethyl citrate, tributyl citrate, acetyl tributyl citrate, triacetin, glycerides, acetylated monoglycerides, oils, mineral oil, castor oil, PEG castor oil, and the like.

Referring again to the embodiment of the invention depicted in FIG. 3, dosage form 10 in its non-swollen state has a length L1 and a maximum diameter D1. FIG. 4 shows dispensing device 10 after having been placed in the stomach.

After swelling, the dosage form 10 has a length L2 and a maximum diameter D2 measured at the widest part of the swollen polymer matrices, as illustrated in FIG. 4. Generally, for human applications the largest dimension of the device in the swollen state equivalent to the diameter D2 should be greater than 7 mm, preferably 10 mm or greater, and most preferably 13 mm or greater during the period of residence in the stomach when active agent is being dispensed. Since the active agent formulation is intended to remain in the stomach for a prolonged period, the effective diameter of the active agent dosage form when in its swollen state in the stomach may have to be significantly larger than 13 mm, and may extend to more that 50 mm or greater. Larger dosage forms may be appropriate particularly when the polymer matrix is designed to erode relatively rapidly over time in order to provide the required delivery of active agent for therapeutic effect.

In contrast to the exposed segments of the swollen polymer matrices, band 18 and the portion of the polymer matrices beneath it do not swell significantly. Accordingly, that segment of the dosage form surrounded by band 18 is maintained in a constrained and more compressed, non-swollen state than the unbanded portion of the matrices. Since band 18 does not take up an appreciable amount of fluid from the stomach and swell, band 18 retains its substantially rigid or semi-rigid form, and provides an element of rigidity to the dosage form as a whole. While it is not entirely clear how band 18 and the constrained segment of the polymer matrices of layers 12 and 14 facilitate retention of the dosage form in the stomach through housekeeping waves, it is thought that the band reduces the rate of erosion of the polymer matrices, thus maintaining a larger effective size of the dosage form and reducing the chance for its expulsion from the stomach, for a longer period of time than would otherwise occur if the band was not present. Additionally, the presence of the band on the polymer matrices provides a semi-rigid segment of the dosage form that appears to permit the dosage form to be retropelled into the main area of the stomach as a reaction to the stomach contractions rather than being expelled by the housekeeping wave, as a less rigid gel would be inclined to be.

For applications in animals other than humans, for example in dogs, the maximum diameter should be greater than about 2 mm. The maximum dimension for any particular dosage form will depend on the particular application and animal in which the device is being used. Such dimensions can be determined by those skilled in the art in accordance with the teaching herein and the various patents and publications noted herein and existing in the related art.

A practical consideration, particularly for oral administration to humans, is that the initial size of the device be such that it can be reasonably, comfortably swallowed. For human oral applications, a preferred size of the device in its form prior to administration to the stomach would be on the order of a size 000 capsule to a size 5 capsule. However, it is understood that smaller or larger sizes could be used for particular applications where necessary. Since the dosage forms of the invention may be gel-forming, it may be desirable to wet the outer surface of the dosage form immediately prior to the subject swallowing the dosage form in order to provide a more slippery outer surface and promote ease of swallowing. Alternatively, the bilayer core can be inserted into a hard gelatin capsule prior to application of the band in order to facilitate swallowing and also promote ease of manufacture in applying and forming the bands. Upon entering the stomach, that portion of the hard gelatin capsule that is not covered by the band will dissolve, exposing the polymer matrices to fluid in the stomach. As the polymers imbibe fluid, the dosage form will swell in the exposed segments: as previously described. The dosage form typically is prepared to allow for swelling at a controlled rate, particularly at a limited initial rate, so that the dosage form does not swell inordinately during the swallowing process and result in obstruction of the esophagus.

The configuration of the multilayer dosage form is selected to achieve the delivery duration and gastric retention period targeted for a particular drug. Generally, the bilayer compressed tablet is fabricated such that the dimensions and proportions of the tablet resemble those of a hard gelatin capsule. For example, where the dosage form is fabricated to dimensions comparable to a size 0 capsule, dimension D1 illustrated in FIG. 3 represents a value of approximately 8 mm. The thickness of the drug layer can be selected such that it represents a range of 0.05D1 to 0.95D1. The drug layer most commonly represents a thickness in the range of 0.2D1 to 0.8D1, with a thickness of 0.5D1 to 0.7D1 being especially preferred. The drug layer may itself be divided into a number of layers (for example, two to four sublayers) and fabricated using conventional multilayer tableting presses. The individual sublayers may be varied in number and thickness, generally within the overall dimensional ranges set forth above, and each sublayer may have varying drug concentrations of the same or different drugs to alter the delivery profile(s) of the drug(s). One or more of the sublayers may be inert if a pulsed delivery of drug is desirable; or, the first, outer sublayer of the drug layer may have a low concentration of drug relative to the next sublayer, and SO on, to provide an ascending profile of drug delivery and each sublayer having a higher concentration of drug than its predecessor is exposed to the environment of use. Other designs of the dosage form to effect particular delivery profiles or periods of drug delivery will be apparent to one skilled in the art.

It is preferred that the dosage forms of this invention be administered when the subject is in the fed state to allow time for maximum swelling of the polymer matrix prior to the housekeeping wave being initiated. Generally a meal size that results in a delay of the housekeeping wave of from about 1 to 3 hours is satisfactory. It may be preferable to administer one or more of the dosage forms at the start of each dosing period, depending on the size of the dosage form, to facilitate swallowing and yet provide sufficient dose of active agent. Particularly in those instances where the dosage form is near the lower end of the size range, i.e., the maximum diameter along the longitudinal axis is on the order of 7–13 mm, it is preferable that the dosage form be administered to the subject in the fed state to allow for significant swelling of the dosage form prior to the housekeeping wave occurring. Typically, administration will occur with the meal or within two hours thereafter, and preferably within one hour of completion of the meal.

Depending on the half-life of an active agent, once-a-day dosing could conveniently occur with or after dinner. For b.i.d. (i.e., twice-a-day) dosing to a human subject, the dosage form can conveniently be administered with or after breakfast and dinner, but, if after, preferably within one or two hours after conclusion of the meal. For more frequent administration, such as t.i.d., the dosage form may be administered after breakfast, lunch and dinner. For administration within usual meal patterns, it is desirable that the subject consume small amounts of food or liquids prior to administration of the dosage form. The dosage form may be administered prior to the taking of food if administered with a sufficient quantity of liquid so as to delay onset of the housekeeping wave, until consumption of food is initiated.

To facilitate retention of the dosage forms of the invention, particularly if the dosage form is to be administered to a subject in the fasted state, it may be desirable to combine one or more gastric-emptying delaying agents with the active agent composition or coat the dosage form with a composition containing a gastric-emptying delaying agent, i.e., a substance that delays onset of the housekeeping wave of the IMMC. Examples of agents for delaying onset of the housekeeping wave, preferably locally delivered by the dosage form in amounts not resulting in any substantial systemic effect to the subject, as for example, anticholinergic agents such as propantheline, and other agents including, but not limited to, methylcellulose, guar gum, fats such as triglyceride esters, e.g., triethanol myristate, fatty acids of 10–15 carbon atoms, and the like.

FIGS. 5 and 6 show dosage form 10 after a length of time in the fluid environment of the stomach. The polymer matrices have eroded at the exposed surfaces of the matrices, i.e., those portions of the matrices not covered by the insoluble material 18 to such an extent that the device 10 is smaller than its initial swollen configuration. Erosion of the matrices will continue to deliver active agent to the stomach until the dosage form has substantially eroded so that no significant amount of active agent remains or has eroded to such an extent that the remainder of the dosage form is expelled from the stomach. Band 18 will be expelled from the stomach either alone if it has separated from the dosage form at some time near the end of the delivery period or as part of the remainder of the dosage form expelled: from the stomach. In some applications, it may be desirable to form band 18 with weakened portions so that band 18 splits and falls away from the polymer matrices after some predetermined time in the stomach to permit a particular release pattern of active agent from the dosage form over the delivery period.

The polymer matrices forming layers 12 and 14 and useful in this invention can be prepared by standard methods from the materials previously described. The following description will be directed to the active agent layer 14; however, the same procedures may be applied for layer 12 by eliminating the active agent.

Typically, for example, an appropriate quantity of an active agent or agents and the polymer ingredients are separately passed through a screen, such as a screen having a mesh of about 40 wires per inch, to reduce any larger sized materials, and dry mixed. Then, a pharmaceutically-acceptable liquid, having a sufficient vapor pressure to allow subsequent drying over a reasonable period of time, for example 24 hours, is added to the dry mixture and the damp mass is extruded through a mesh screen (e.g. 20 wires per inch) to further mix the materials. Examples of suitable liquids are water, methanol, ethanol, isopropanol, acetone, ethyl acetate, and the like. After the extrusion process, the mixture is allowed to dry, for example in air overnight at room temperature if the active agent does not require any special handling. After drying, the resulting material is granulated, for example by passing the dried material through a mesh screen (e.g., 20 wires per inch). The granules are combined with a suitable tableting lubricant which has been previously passed through a mesh screen (e.g., 60 wires per inch). The resulting material is tumbled to produce the finished granulation for the tableting process. Tablets are produced using well known methodologies associated with horizontal and vertical compression units using dies and punches of appropriate dimensions. Alternate granulation methods, for example, fluid bed granulation or direct compression granulation can be used as well and such method will be chosen by one skilled in the art depending on the particular nature of the materials being used and the convenience and preference of the fabricator. To form the laminated structure of the dosage form, either the granulated first layer 12 or the second layer 14 is first compressed in an appropriately sized tableting mold, and then the other granulated layer is added to the same mold over the compressed layer and compressed to form the bilayer laminated core.

While the foregoing process has been described with respect to dry ingredients, including the active agent, methodologies for active agents in other than the solid state can be employed. For example, if the active agent is not crystalline, but is in liquid form, the active agent may first be encapsulated as microcapsules to provide a solid that can be fabricated a described above. Microencapsulation of the liquid active agent can be accomplished by standard encapsulation techniques including, for example, spray coating, spray drying encapsulation, centrifugal suspension, and phase inversion techniques as described in *Polymeric Delivery Systems—Properties and Applications*, ACS Symposium Series 520, edited by El-Nokaly, Piatt and Charpentier (1993), which is incorporated herein by reference. Additionally, liquid active agents can be absorbed into porous clays and polymers and then further incorporated into the polymer matrix of the dosage form.

In certain applications where it is desirable to dispense an active agent as a liquid or in a liquid state, it has been found convenient to sorb the liquid, active agent formulation into porous particles which are then formulated into the polymer matrix. Materials useful for sorbing the liquid, active agent formulations are porous particulates that are characterized by high compressibility or tensile strength to withstand compacting forces applied during compacting steps and minimize exudation of liquid, active agent formulation from the pores; low friability so as to preclude or minimize exudation of the liquid, active agent formulation from the particles during compacting steps; and high porosity so as to absorb an adequate of amount of a liquid, active agent formulation to provide an effective amount of active agent in a dosage form. The particles should be adapted to absorb an amount of liquid, active agent formulation such that a therapeutically effective amount of the active agent may be delivered in a unitary dosage form that is of a size that can be conveniently swallowed by a subject and, preferably provided in four or fewer tablets or capsules for ingestion at the same time. The porosity of the particles should be such that at least 5% by weight of the liquid, active agent formulation, based on the total weight of the particle may be sorbed into the pores of the particles, while the particles exhibit sufficient strength at such degree of active agent loading so as not to significantly be crushed or pulverized by compacting forces to which the particles may be subjected during manufacturing operations. Up to 50% by weight of the liquid, active agent formulation may be sorbed into crystalline porous particles, such as calcium hydrogen phosphate, but more typically 30–40%. Greater amounts of liquid, active agent formulation may be sorbed into the amorphous particles, such as the magnesium aluminometasilicates.

Preferred materials are those having a strength to resist compression forces of greater than 1500 kg/cm² without substantial exudation of the liquid, active agent formulation, and most preferably without the tablet hardness plateauing.

A particularly suitable porous particle is exemplified by the particular form of calcium hydrogen phosphate described in U.S. Pat. No. 5,486,365, which is incorporated herein by reference. As described therein, calcium hydrogen phosphate is prepared by a process yielding a scale-like calcium hydrogen phosphate that can be represented by the formula $CaHPO_4 \cdot mH_2O$ wherein m satisfies the expression $0 \leq m \leq 2.0$. The scale-like calcium hydrogen phosphate produced has characteristic physical properties that make it particularly suitable for use in the present invention. The scale-like material provides high specific surface area, high specific volume, high capacity for water and oil absorption, and the ability to readily form into spheres Upon spray drying. The spherical particulates have excellent flow properties and permit compaction in the carrier matrix without significant e crushing or pulverizing of the particles during the compaction step.

The scale-like calcium hydrogen phosphate particles generally have a BET specific surface area of at least 20 m²/g, typically 20 m²/g–60 m²/g, a specific volume of at least 1.5 ml/g, typically 2–5 ml/g or more, and an oil and water absorption capacity of at least 0.7 ml/g, typically 0.8–1.5 ml/g. When formed into spheres the spherical particulates may have a mean particle size of at least 70 microns, usually about 70–130 microns, and often about 90–120 microns. The particle size distribution may be 100% through 40 mesh, 50%–100% through 100 mesh, and 20%–40% through 200 mesh. The bulk density may be from about 0.4 g/ml–0.6 g/ml.

A most preferred form of calcium hydrogen phosphate is that sold under the trademark FujiCalin® by Fuji Chemical Industries (U.S.A.) Inc., Englewood, N.J., in types SG and S. Typical parameters for that material include a mean pore size on the order of 70 Angstroms, a mean particle size of about 110 microns, a specific volume of about 2 ml/g, a BET specific surface area of about 30–40 m²/g, and an oil and water absorption capacity of about 0.8 ml/g. Type SG typically will have a particle size distribution of 100% through 40 mesh, 60% through 100 mesh and 20% through 200 mesh. Type S typically will have a particle size distribution of 100% through 40 mesh, 90% through 100 mesh and 60% through 200 mesh. Mixtures of the two types may be conveniently employed to provide particulates having physical characteristics that are suitable for various applications, as may be determined by those skilled in the art of pharmaceutical formulation, tableting and manufacturing.

The calcium hydrogen phosphate has low friability, demonstrating a tensile strength of up to about 130 Kg/cm² when subjected to compressive forces of up to 3000 Kg/cm². The angle of repose for the preferred materials typically is on the order of 32–35 degrees.

Another material that may be utilized is that formed of magnesium aluminometasilicate which may be represented by the general formula

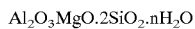
$Al_2O_3 MgO \cdot 2SiO_2 \cdot nH_2O$ wherein n satisfies the relationship $0 \leq n \leq 10$. Commercially available magnesium aluminometasilicates are sold as Grades $S_1$, $SG_1$, $UFL_2$, $US_2$, $FH_1$, $FH_2$, $FL_1$, $FL_2$, S2, $SG_2$, $NFL_2N$, and $NS_2N$, under the trademark Neusilin™ by Fuji Chemical Industries (U.S.A.) Inc., Englewood, N.J. Especially preferred grades are $S_1$, $SG_1$, $US_2$ and UFL2. Those materials are amorphous and typically have a specific surface area (area) of about 100–300 m²/g, an oil absorption capacity of about 1.3–3.4 ml/g, a mean particle size of about 1–2 microns, an angle of repose about 25°–45°, a specific gravity of about 2 g/ml and a specific volume of about 2.1–12 ml/g.

Other absorptive materials may be substituted for the foregoing. For example, powders of microcrystalline cellulose sold under the tradenames Avicel (FMC Corporation) and Elcema (Degussa), porous sodium carboxy methylcellulose cross-linked sold as Ac-Di-Sol (FMC Corporation), porous soy bean hull fiber sold under the trade name Fl-1 Soy Fiber (Fibred Group), and porous agglomerated silicon dioxide, sold under the tradenames Cab-O-Sil (Cabot) and Aerosil (Degussa), may be used.

The liquid, active agent formulation may be in any form that can be dispensed from the inside of the pores as the drug layer disintegrates in the environment of use. The formulation, for example, may be neat, liquid active agent, liquid active agent in a solution, suspension, emulsion or self-emulsifying composition, or the like, or a liposomal solution or solid formulation, or solid active agent in solution, suspension or slurry. Optionally other dosage-forming ingredients, such as an anti-oxidant, a suspending agent, a surface active agent, and the like may be present in the liquid, active agent formulation. The liquid, active agent formulation will be released in a form most suitable to provide active agent to the site of delivery in a state in which it may be rapidly absorbed in the environment of use to provide its beneficial action with minimum delay once delivered to the absorption site.

The present invention may have particular utility in the delivery of liquid, active agent formulations that are in the form of emulsions or self-emulsifying compositions. The term emulsion as used in this specification denotes a two-phase system in which one phase is finely dispersed in the other phase. The term emulsifier, as used by this invention, denotes an agent that can reduce and/or eliminate the surface and the interfacial tension in a two-phase system. The emulsifier agent, as used herein, denotes an agent possessing both hydrophilic and lipophilic groups in the emulsifier agent. The term microemulsion, as used herein, denotes a multicomponent system that exhibits a homogenous single phase in which quantities of a drug can be solubilized. Typically, a microemulsion can be recognized and distinguished from ordinary emulsions in that the microemulsion is more stable and usually substantially transparent. The term solution, as used herein, indicates a chemically and physically homogenous mixture of two or more substances.

The emulsion formulations of active agent generally comprise 0.5 wt % to 99 wt % of a surfactant. The surfactant functions to prevent aggregation, reduce interfacial tension between constituents, enhance the free-flow of constituents, and lessen the incidence of constituent retention in the dosage form. The therapeutic emulsion formulations useful in this invention may comprise a surfactant that imparts emulsification comprising a member selected from the group consisting of polyoxyethylenated castor oil comprising 9 moles of ethylene oxide, polyoxyethylenated castor oil comprising 15 moles of ethylene oxide, polyoxyethylene castor oil comprising 20 moles of ethylene oxide, polyoxyethylenated castor oil comprising 25 moles of ethylene oxide, polyoxyethylenated castor oil comprising 40 moles of ethylene oxide, polyoxylenated castor oil comprising 52 moles of ethylene oxide, polyoxyethylenated sorbitan monopaimitate comprising 20 moles of ethylene oxide, polyoxyethylenated sorbitan monolaurate comprising 20 moles of ethylene oxide, polyoxyethylenated sorbitan monolaurate comprising 20 moles of ethylene oxide,polyoxyethylenated sorbitan monooleate comprising 20 moles of ethylene oxide, polyoxyethylenated sorbitan monostearate comprising 4 moles of ethylene oxide, polyoxyethylenated sorbitan tristearate comprising 20 moles of ethylene oxide, polyoxyethylenated sorbitan monostearate comprising 20 moles of ethylene oxide, polyoxyethylenated sorbitan trioleate comprising 20 moles of ethylene oxide, polyoxyethylenated stearic acid comprising 8 moles of ethylene oxide, polyoxyethylene lauryl ether, polyoxyethylenated stearic acid comprising 40 moles of ethylene oxide, polyoxyethylenated stearic acid comprising 50 moles of ethylene oxide, polyoxyethylenated stearyl alcohol comprising 2 moles of ethylene oxide, and polyoxyethylenated oleyl alcohol comprising 2 moles of ethylene oxide. The surfactants are available from Atlas Chemical Industries, Wilmington, Del.; Drew Chemical Corp., Boonton, N.J.; and GAF Corp., New York, N.Y.

Typically, an active agent emulsified formulation useful in the invention initially comprises an oil phase. The oil phase of the emulsion comprises any pharmaceutically acceptable oil which is not miscible with water. The oil can be an edible liquid such as a non-polar ester of an unsaturated fatty acid, derivatives of such esters, or mixtures of such esters can be utilized for this purpose. The oil can be vegetable, mineral, animal or marine in origin. Examples of non-toxic oils comprise a member selected from the group consisting of peanut oil, cottonseed oil, sesame oil, olive oil, corn oil, almond oil, mineral oil, castor oil, coconut oil, palm oil, cocoa butter, safflower, a mixture of mono- and di-glycerides of 16 to 18 carbon atoms, unsaturated fatty acids, fractionated triglycerides derived from coconut oil, fractionated liquid triglycerides derived from short chain 10 to 15 carbon atoms fatty acids, acetylated monoglycerides, acetylated diglycerides, acetylated triglycerides, olein known also as glyceral trioleate, palmitin known as glyceryl tripalmitate, stearin known also as glyceryl tristearate, lauric acid hexylester, oleic acid oleylester, glycolyzed ethoxylated glycerides of natural oils, branched fatty acids with 13 molecules of ethyleneoxide, esters of saturated coconut and palm kernal fatty acids, caprylic and capric acid with glycerol or propylene glycol such as Miglyols supplied by Hulls America, Somerset, N.J., and oleic acid decylester. The concentration of oil, or oil derivative in the emulsion formulation is 1 wt % to 40 wt %, with the wt % of all constituents in the emulsion preparation equal to 100 wt %. The oils are disclosed in *Pharmaceutical Sciences* by Remington, 17$^{th}$ Ed., pp. 403–405, (1985) published by Mark Publishing Co., in *Encyclopedia of Chemistry*, by Van Nostrand Reinhold, 4$^{th}$ Ed., pp. 644–645, (1986) published by Van Nostrand Reinhold Co.; and in U.S. Pat. No. 4,259,323 issued to Ranucci.

Dosage forms of this invention may be utilized to delivery liquid formulations such as contained in immediate-release, commercially-available dosage forms over a prolonged period of time. Examples of commercially available encapsulated liquid formulations that may be utilized include, inter alia, Placidyl® brand of ethchlorvynol, Adalat® brand of nifedipine, VePesid® brand of etoposide, Lanoxicaps® brand of digoxin, Zantac® brand of ranitidine hydrochloride, Sandimmune® and Neoral® brands of cyclosporin, Calderol® brand of calcifediol, Zarontin® brand of ethosuximide, Procardia® brand of nifedipine, Rocaltrol® brand of calcitriol and Vescenoid® brand of tretinoin.

The dosage form may contain an antioxidant to slow or effectively stop the rate of any autoxidizable material present in the dosage form. Representative antioxidants comprise a member selected from the group of ascorbic acid; alpha tocopherol; ascorbyl palmitate; ascorbates; isoascorbates; butylated hydroxyanisole; butylated hydroxytoluene; nordihydroguiaretic acid; esters of garlic acid comprising at least 3 carbon atoms comprising a member selected from the group consisting of propyl gallate, octyl gallate, decyl gallate, decyl gallate; 6-ethoxy-2,2,4-trimethyl-1,2-dihydro-guinoline; N-acetyl-2,6-di-t-butyl-p-aminophenol; butyl tyrosine; 3-tertiarybutyl-4-hydroxyanisole; 2-tertiary-butyl-4-hydroxyanisole; 4-chloro-2,6-ditertiary butyl phenol; 2,6-ditertiary butyl p-methoxy phenol; 2,6-ditertiary butyl-p-cresol: polymeric antioxidants; trihydroxybutyro-phenone physiologically acceptable salts of ascorbic acid, erythorbic acid, and ascorbyl acetate; calcium ascorbate; sodium ascorbate; sodium bisulfite; and the like. The amount of antioxidant used for the present purposes is about 0.001% to 25% of the total weight of the composition present in the dosage form. Antioxidants are known to the prior art in U.S. Pat. Nos. 2,707,154; 3,573,936; 3,637,772; 4,038,434; 4,186,465 and 4,559,237.

The dosage form may also contain a chelating agent to protect the active agent either during storage or when in use. Examples of chelating agents include, for example, polyacrylic acid, citric acid, edetic acid, disodium edetic acid, and the like. The chelating agent may be co-delivered with the active agent in the environment of use to preserve and protect the active agent in situ. Protection is provided for active agents which are inactivated by chelation with multivalent metal cations such as calcium, magnesium or aluminum that may be present in some foods and are at natural background levels in the fluids of the gastrointestinal tract. Such chelating agents may be combined with the liquid, active agent formulation in the porous particles, or the chelating agents may be incorporated into the matrix in which the porous particles are dispersed.

The liquid formulation may also comprise a surfactant or a mixture of surfactants where the surfactant is selected from the group consisting of nonionic, anionic and cationic surfactants. Exemplary nontoxic, nonionic surfactants suitable for forming a composition comprise alkylated aryl polyether alcohols known as Triton®; polyethylene glycol tertdodecyl throether available as Nonic®; fatty and amide condensate or Alrosol®; aromatic polyglycol ether condensate or Neutronyx®; fatty acid alkanolamine or Ninol® sorbitan monolaurate or Span®; polyoxyethylene sorbitan esters or Tweens®; sorbitan monolaurate polyoxyethylene or Tween 20®; sorbitan mono-oleate polyoxyethylene or Tween 80®; triblock copolymers polyoxyethylenepolyoxypropylene-polyoxyethylene also known as Pluronics®; polyglycolyzed glycerides such as Labrasol, PEG-8 glyceryl caprylate/caprate, PEG-4 glyceryl caprylate/caprate, polyglyceryl-3 isostearate, PEG-6 glyceryl monooleate, PEG-6 glyceryl linoleate, PEG-32 palmito stearate, PEG-32 glyceryl stearate, saccharose distearate, saccharose mono-di stearate, saccharose monoplamitate, glyceryl monolaurate, lmwitors, Softisans and Dynasans as supplied by Hulls America, Somerset, N.J., polyoxyethylated castor oil such as Cremophor and polyoxypropylene-polyoxyethylene. By way of example, anionic surfactants comprise sulfonic acids and the salts of sulfonated esters such as sodium lauryl sulfate, sodium sulfoethyl oleate, dioctyl sodium sulfosuccinate, cetyl sulfate sodium, myristyl sulfate sodium; sulated esters; sulfated amides; sulfated alcohols; sulfated ethers; sulfated carboxylic acids; sulfonated aromatic hydrocarbons; sulfonated ethers; and the like. The cationic surface active agents comprise cetyl pyridinium chloride; cetyl trimethyl ammonium bromide; diethylmethyl cetyl ammonium chloride; benzalkonium chloride; benzethonium chloride; primary alkylamonium salts; secondary alkylamonium salts; tertiary alkylamonium salts; quaternary alkylamonium salts; acylated polyamines; salts of heterocyclic amines; palmitoyl carnitine chloride, behentriamonium methosulfate, and the like. Generally, from 0.01 part to 1000 parts by weight of surfactant, per 100 parts of active agent is admixed with the active agent to provide the active agent formulation. Surfactants are known to the prior art in U.S. Pat. Nos. 2,805,977; and in 4,182,330.

The liquid formulation may comprise permeation enhancers that facilitate absorption of the active agent in the environment of use. Such enhancers may, for example, open the so-called "tight junctions" in the gastrointestinal tract or modify the effect of cellular components, such a p-glycoprotein and the like. Suitable enhancers include alkali metal salts of salicyclic acid, such as sodium salicylate, caprylic or capric acid, such as sodium caprylate or sodium caprate, diethylene glycol monoethyl ether, propylene glycol laurate, and the like. Enhancers may include the bile salts, such as sodium deoxycholate. Various p-glycoprotein modulators are described in U.S. Pat. Nos. 5,112,817 and 5,643,909, which are incorporated herein by reference. Various other absorption enhancing compounds and materials are described in U.S. Pat. No. 5,824,638, which also is incorporated herein by reference. Enhancers may be used either alone or as mixtures in combination with other enhancers.

The liquid, active agent formulation of the dosage form may optionally be formulated with inorganic or organic acids or salts of drugs which promote dissolution and disintegration or swelling of the porous particles upon contact with biological fluids. The acids serve to lower the pH of the microenvironment at the porous particle, and promote rapid dissolution of a particle, such as calcium hydrogen phosphate, that is soluble in low pH environments, thus providing rapid liberation of the liquid, active agent formulation contained in the porous particle. Examples of organic acids include citric acid, tartaric acid, succinic acid, malic acid, fumaric acid and the like. Salts of drugs where the anion of the salt is acidic, such as acetate, hydrochloride, hydrobromide, sulfate, succinate, citrate, and the like, can be utilized to produce immediate disintegration and dissolution of the porous particle. A more complete list of acidic components for this application is provided in Journal of Pharmaceutical Sciences, "Pharmaceutical Salts", Review Articles, January, (1977), Vol. 66, No. 1, pages 1–19. The interaction of an acidic component with a porous particle of, for example, calcium hydrogen phosphate, in the presence of water from gastric fluids accelerates dissolution of the particle at a greater rate than gastric fluid alone, producing a more rapid and complete release of the liquid, active agent formulation into the environment of use. Likewise alkaline components or salts of drugs where the cation of the salt is alkaline such as choline may be incorporated into the liquid, active agent formulation to promote rapid and complete dissolution of a porous particle which is soluble or swells at elevated pH. Such a particle may be formed, for example, of poly(methacrylic acid-methyl methacrylate) 1:2 available commercially as Eudragit S100 (Rohm America, Sommerset, N.J.

In order to prepare a dosage form of the present invention, the first layer 12 typically is prepared by granulation and tableting methods described previously and which are conventionally described in Remington's Pharmaceutical Sciences, Eighteenth Edition (1990). Then, the active agent layer 14 is prepared and laminated onto layer 12, to provide a dosage form of the desired size and shape. In its initial prepared form, the dosage form is about the size and dimensions of a size "000" to size 5 hard gelatin capsule. The cross-sectional shape of the matrix may be circular or may be oval, triangular, square, hexagonal or other shapes that are easily handled, especially by patients with limited dexterity. Presently preferred shapes are those in which the cross-section is circular or oval. The bands are then placed onto the surface of active agent formulation matrix or printed onto the surface using conventional banding or printing techniques, such as disclosed herein or in U.S. Pat. No. 5,534,263, which is incorporated herein by reference.

As described above, the active agent itself may be in liquid, solid or semisolid form. The active agent formulation may contain additional materials and may be designed in a multitude of ways to provide a specific active agent delivery profile. In one embodiment the active agent is capable of slow dispersion or dissolution in the stomach. In another embodiment, the polymer matrix of layer 14 may contain a surfactant so that the formulation is more readily susceptible to erosion in the stomach. In still another embodiment, the formulation of layer 14 may include a solid surfactant and provide active agent delivery in a finely dispersed form. In yet another embodiment, formulation layer 14 may include a lipidic or wax matrix that erodes as the active agent is released. In yet a further embodiment, the formulation may include coated microspheres of an active agent or microspheres of an active agent and an adjuvant. The active agent either alone or with adjuvant can be delivered simultaneously from the microspheres either by diffusion or by osmosis. Suitable materials useful as active agent carriers and excipients are known in the art and are disclosed in U.S. Pat. Nos. 4,595,583 and 4,874,388, for example. For active agents that may tend to degrade in the stomach, the active agent can be enterically coated to protect the active agent it passes to the small intestine in accordance with conventional coating methods.

The dispensing devices of the invention find use, for example, in humans or other animals. The environment of use is a fluid environment and for the purposes of this invention primarily includes the fluid environment of the stomach and the upper intestinal tract or small intestine. A single dispensing device or several dispensing devices can be administered to a subject during a therapeutic program.

The terms "active agent" and "drug" are used interchangeably herein and refer to an agent, active agent, compound, composition of matter or mixture thereof which provides some pharmacologic, often beneficial, effect. This includes foods, food supplements, nutrients, drugs, antiacids, vitamins such as, for example, Vitamin C, Vitamin E, microorganism attenuators and other agents that benefit the environment of use. As used herein, the terms include any physiologically or pharmacologically active substance that produces a localized or systemic effect or effects in animals, including warm blooded mammals, humans and primates; domestic household or farm animals such as cats, dogs, sheep, goats, cattle, horses and pigs; laboratory animals such as mice, rats and guinea pigs; zoo and wild animals; and the like. The active agent that can be delivered includes inorganic and organic compounds, including, without limitation, active agents which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system.

Suitable active agents may be selected from, for example, proteins, enzymes, enzyme inhibitors, hormones, polynucleotides, nucleoproteins, polysaccharides, glycoproteins, lipoproteins, peptides, polypeptides, steroids, hypnotics and sedatives, psychic energizers, tranquilizers, anticonvulsants, antidepressants, muscle relaxants, antiparkinson agents, analgesics, immunosuppressants, anti-inflammatories, antihistamines, local anesthetics, muscle contractants, antimicrobials, antimalarials, antivirals, antibiotics, antiobesity agents, antidiabetic agents, hormonal agents including contraceptives, sympathomimetics, polypeptides and proteins capable of eliciting physiological effects, diuretics, lipid regulating agents, antiandrogenic agents, antiparasitics, neoplastics, antineoplastics, antihyperglycemics, hypoglycemics, nutritional agents and supplements, growth supplements, fats, ophthalmics, antienteritis agents, electrolytes and diagnostic agents.

Examples of active agents useful in this invention include prochlorperazine edisylate, ferrous sulfate, albuterol, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, metformin, methylphenidate hydrochloride, acrivastine, benazepril, carbamazipine, chlorothiazide, desmopressin, dicumarol, furosemide, gepirone griseofulvin, levodopa/benserazide, Ilithium, methylphenidate, 8-methoxalen, metoprolol, misoprostol, octreotide, phenobarbital, phenytoin, piretanide, paraastatin, propoxyphen, riboflavin, sertaline, spironolactone, sumatriptan, ticlopidine, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, nifedipine, methazolamide, bendroflumethiazide, chlorpropamide, glipizide, glyburide, gliclazide, tobutamide, chlorproamide, acetohexamide, troglitazone, orlistat, bupropion, nefazodone, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, prednisolone, 17-β-hydroxyprogesterone acetate, 19-nor-progesterone, norgestrel, norethindrone, norethisterone, norethiederone, progesterone, norgesterone, norethynodrel, terfandine, fexofenadine, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, carbidopa, carbidopa/levodopa, selegiline, chlorpromazine, methyldopa, dihydroxyphenylalanine, calcium gluconate, ketoprofen, ibuprofen, colchicine, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptyline, and imipramine, and pharmaceutical salts of these active agents. Further examples are proteins and peptides which include, but are not limited to, cyclosporins such as cyclosporine A, insulin, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

The present invention is particularly useful to deliver active agents that are poorly absorbed in the lower gastrointestinal tract, but well absorbed in the upper gastrointestinal tract (i.e., the small intestine) or active agents that exhibit poor solubility such that the increased retention time in the stomach allows for a greater quantity of active agent to dissolve from the dosage form than would otherwise be dissolved. Typically, antiviral, antifungal and antibiotic agents, e.g. sulfonamides, quinolones, penicillins, cephalosporins, aminoglycosides, and tetracyclines, are representative classes of agents for which the invention is particularly useful. Such antibiotic agents may include, for example, β-lactam antibiotics, vancomycin, clidamycin, erthromycin, clarithromycin, 14-hydroxy clarithromycin, azithromycin, roxithromycin, dirithromycin, trimethoprim-sulfamethoxaazole, rifampin, ciprofloxacin, amoxicillin, clindamycin, ceftriaxone, cefotaxime, chloramphenicol, clindamycin, cefoxitin, doxycycline, spectinomycin, ofloxacin, rifampin, minocycline, doxycycline, aztreonam, imipenem, meropenem, nitrofurantoin, azithromycin, atovaquone, trimetrexate, dapsone, primaquin, trimetrexate, ketoconazole, floconazole, amphotericin B, itraconazole, trifluridine, foscarnet, zidovudine amantadine, interferon alfa, sulfonamides such as sulfisoxazole, sulfadiazine, and sulfasalazine, quinolones and fluoroquinolones such as, for example, cinoxacin, forfloxacin, diprofloxacin, ofloxacin, spardlosxacin, lomefloxacin, fleroxacin, pefloxacin and amifloxacin, gentamicin, tobramycin, amikacin,netilmicin, kanamycin,and neomycin. Representative antiviral agents include acyclovir, famciclovir, foscarnet, ganciclovir, ritonavir, idoxuridine, sorivudine, trifluridine, valacylcovir, vidarabine, didanosine, stavudine, zalcitabine, zidovudine, amantadine, interferons, e.g., interfon alpha, ribavirin, rimantadine, nucleoside RT inhibitors, such as lamivudine and adeforvir, non-nucleoside inhibitors such as nevrapine, delavairidine, Iviride, saquinavir and indinavir, nucleoside DNAp inhibitors such as famciclovir, fialuridine, cidofovir and lobucavir, antisense oligonucleotides such as afovirsen, receptor decoys such as sICAM-1, capsid binding agents such as pirodavir, and neuraminidase inhibitors such as GG167.

Specific examples of active agents that are readily absorbed in the upper gastrointestinal tract relative to the lower gastrointestinal tract are acyclovir, ganciclovir, cimetidine, ranitidine, captopril, methyldopa, selegiline and the like. Specific examples of active agents that exhibit poor solubility in water are diphenidol, meclizine hydrochloride, hydralazine, prochloperazine maleate, phenoxybenzamine, triethylperazine maleate, anisindone, diphenadione erythrityl tetranitrate, digoxin, isofilurophate, acetazolamide, methazolamide, bendroflumethiazide, chlorpropamide, tolazamide, chlormadionone acetate, phenaglycodol, allopurinol, alluminum aspirin, methotrexate, acetyl sulfisoxazole, erythromyciin, progestins, esterogenic, progestational corticosteroids, hydrocortisone, hydrocorticosterone acetate, cortisone acetate, tramcinolone, methyltesterone, 17-beta-estradiol, ethinyl estradiol, prazosin hydrochloride, ethinyl estradiool 3-methyl ether, pednisolone, 17-alpha-hydroxyprogesterone acetate, 19-norprogesterone, norgestrel, norethindrone, progesterone, norgesterone, norethlynodrel, and the like.

Retention of the device of the present invention in the stomach for a prolonged period of time make it especially useful for the localized treatment of gastric acidity and gastrointestinal disorders such as duodenal ulcers, peptic ulcers and chronic gastritis, particularly those resulting from the presence of Helicobacter pylori. Representative active agents for such uses include cimetidine, rantitidine, famotidine, nizatidine, zolentine, omeprazole, lansoprazole and active agents useful for the treatment of Helicobacter pylori, such as metronidazole, timidazole, amoxicillin, clarithromycin, minocycline and tetracycline.

While for reasons of efficacy, safety, economy, convenience and/or efficiency it may be desirable to utilize a single active agent in the active agent formulation, it is to be understood that more than one active agent may be incorporated into the active agent formulation in a device of this invention, and that the use of the term "agent" or "active agent" in no way excludes the use of two or more such agents or active agents. The agents can be in various forms, such as uncharged molecules, components of molecular complexes or nonirritating, pharmacologically acceptable salts. Also, simple derivatives of the agents (such as prodrugs, ethers, esters, amides, etc) which are easily hydrolyzed by body pH, enzymes, etc, can be employed. Combinations of two or more active agents can optionally be co-delivered, simultaneously or sequentially from the dosage form of this invention. For simultaneous delivery of two or more active agents, the active agents will typically be uniformly dispersed throughout the dosage form. For sequential delivery, different active agents can be selectively placed within the dosage form during its manufacture, as by using the multilaminate structure for layer 14 described previously. Alternatively, a core that contains one active agent can be prepared, and the core coated or formed with an outer layer containing a second active agent. Initially, the agent in the outer portion of the dosage form will be dispensed, and as the dosage form erodes in the stomach, the second active agent will be dispensed at a later time.

The active agent dosage form may include additional ingredients, such as, for example, a buffer or other agents for controlling pH in the stomach or elsewhere in the gastrointestinal tract, an agent or agents for delaying onset of the housekeeping wave, preferably locally delivered by the dosage form in amounts not resulting in any substantial systemic effect to the subject, as for example, anticholinergic agents such as propantheline, and other agents including, but not limited to, methylcellulose, guar gum, fats such as triglyceride esters, e.g., triethanol myristate, fatty acids of 10–15 carbon atoms, and the like, a viscosity regulating vehicle, a surfactant, a dye, a permeation enhancer, a proteinase inhibitor, or other formulation ingredients and additives, as are known in the art. The active agent dosage form may also include minor amounts of polymers which serve useful functions in tablet formation, for example, to improve the tablet cohesiveness after compression or to improve the physical or chemical stability of the dosage form. These polymers are added at quantities less than 10% by weight and preferably less that 5% by weight of the tablet. Examples of such polymers include hydroxypropyl methyl cellulose having molecular weights of less that 20,000 grams per mole, methycellulose having a molecular weight of less than 20,000 grams per mole, polyvinyl pyrrolidone having a molecular weight of less than 360,000 grams per mole, and the like.

The amount of active agent employed in the delivery device will be that amount necessary to deliver a therapeutically effective amount of the agent to achieve the desired therapeutic result, and may range from 1 ng to 2500 mg, although lower and higher amounts may be used in particular circumstances. In practice, this will vary widely depending upon the particular agent, the degree of active agent absorption, the severity of the condition, and the desired therapeutic effect. Thus, it is not practical to define a particular range for the therapeutically effective amount of each active agent incorporated into the device. Such ranges can easily be determined by one skilled in the art using conventional methods, for example from dose ranging and plasma level studies. Any references to specific quantities of active agent or specific dose ranges of active agent herein are intended to include the amount or amounts of active agent specified and bioequivalents thereof.

When the delivery device of this invention is being used to substitute for one or more doses of an active agent presented in a conventional dosage form that is usually prescribed for multiple dosing during a predetermined period, the sum of the amounts of active agent present in the multiple doses of the conventional dosage form for use in the period may be used to determine an upper limit on the of the amount of active agent to be included in the device of this invention. For example, if the conventional dosage form contains 200 mg of active agent and is to be administered every 3 hours, a dosage form of this invention may be prepared for administration every 6 hours, and that dosage form may contain 400 mg of active agent which will be delivered over the 6 hour period.

However, when compliance with multiple dosing is a problem, the advantage of administering the dosage forms of the invention at fewer times throughout a twenty-four hour period may provide incentive to incorporate greater amounts of active agent, where such greater amounts do not have any deleterious effects. The specific amount of active agent to be included in the dosage form of the invention can easily be determined by routine dosage studies that compare the blood plasma active agent levels of subjects with conventional dosing and the dosage form of this invention.

The dosage forms of this invention can conveniently release active agent in a controlled and sustained manner over a prolonged period. Typically, active agent will be released from the dosage form at a rate that releases a therapeutically effective amount of active agent to the subject over a substantial portion of the period between administration of the dosage forms. Typically, release will occur over 40% of the period between repeated administration of the dosage form, more preferably at least over 60% of the period, and most preferably over 80% of the period. Dosage forms that result in a $C_{max}$ of the active agent in the plasma of the subject being reached within 1–2 hours, and maintained for a prolonged period, preferably, 4–6 hours, may be particularly useful.

In an especially preferred embodiment, the invention comprises a first layer 12 having a composition of 60–100 percent of a water soluble, polyethylene oxide polymer having a molecular weight between about 900,000 and 10,000,000, and a drug layer 14 having from about 10 weight percent to about 50 weight percent of a water-soluble polyethylene oxide polymer having a molecular weight between about 100,000 and 600,000 and from about 10 weight percent to about 60 weight percent of a water-insoluble hydroxypropyl cellulose polymer. The hydroxypropyl cellulose polymer preferably has a hydroxypropyl content of between about 8–15 weight percent, and most preferably between about 10–13 weight percent. The composition of this invention is useful to prepare the active agent dosage forms described herein, and finds particular utility with respect to the antiviral, antimicrobial, antidiabetic, antihyperglycemic, hypoglycemic, antidepressant, antiobesity, and antifungal active agents described herein.

The following examples are illustrative of the present invention. They are not to be construed as limiting the scope of the invention. Variations and equivalents of these examples will be apparent to those skilled in the art in light of the present disclosure, the drawings and the claims herein. In particular, variations in the dosage forms described that are bioequivalent are considered within the scope of the present invention.

PREPARATION 1

An example of a active agent which requires frequent dosing is acyclovir. A typical dosing regimen for this antiviral active agent is five doses per day administered every four hours. A dosage form in accordance with this invention for twice daily dosing of acyclovir is formulated according to the following procedures. The dosage form is retained in the stomach and releases acyclovir over a prolonged period of time.

22.5 Grams of acyclovir and 3.6 grams of the gel-forming polymer polyethylene oxide, having a number average molecular weight of approximately 200,000 grams per mole, are separately screened through a mesh having 40 wires per inch. The polyethylene oxide is supplied under the trade name Polyox® grade WSR N80 as manufactured by Union Carbide Corporation, Danbury, Conn. The sized active agent and polymer are dry mixed. Then, 3.75 grams of a hydroattractant water-insoluble polymer, hydroxypropyl cellulose having a hydroxypropyl content of 10–13 weight percent and an average fiber particle size of 50 microns, is sieved through the 40-mesh screen and blended into the mixture. The hydroxypropyl cellulose is supplied as Low-Substituted Hydroxypropyl Cellulose grade 11 as manufactured by Shin-Etsu Chemical Company, Ltd., Tokyo, Japan. Anhydrous ethyl alcohol, specially denatured formula 3A, i.e., ethanol denatured with 5 volume percent methanol, is added to the mixture with stirring until a uniformly damp mass formed. This damp mass is extruded with pressure through a screen having 20 wires per inch. The extrudate is then allowed to air dry at room temperature overnight. After drying, the resulting extrudate is passed again through the 20-mesh sieve, forming granules. 0.15 Grams of the tableting lubricant, magnesium stearate, are passed through a sieve having 60 wires per inch. The sized 60-mesh lubricant is then tumbled into the granules to produce the finished drug layer granulation.

A separate granulation is prepared by passing 29.85 grams of a different gel-forming polyethylene oxide through a mesh having 20 wires per inch. The polyethylene oxide has a molecular weight of approximately 7 million and is supplied as Polyox grade WSR-303. 0.15 Grams of magnesium stearate sized through a 60 mesh screen is tumbled into the 20 mesh Polyox 303, to produce the finished retention-layer granulation.

800 Milligram portions of the resulting drug layer granulation and 250 mg portions of the retention-layer granulation are weighed and compacted with caplet-shaped tooling on a Carver press at pressure head of 1.5 tons to a target tablet weight, e.g., each approximately 1050 mg. The shape of the tablet has approximately cylindrical proportions, for example, the diameter is approximately 7.6 millimeters (mm) and the length approximately 22 mm. Such dosage form contains a unit dose of 600 mg acyclovir.

A tube of polyolefin material having an outside diameter of 7.7 mm and having a wall thickness of 0.25 mm is sliced with a razor to produce rings. The width of each ring was approximately 3 mm. One ring is then press fitted onto each caplet such that the ring, or band, is located approximately at the midpoint of the length of the caplet. This step completes the fabrication procedure of the acyclovir banded caplet. The acyclovir dosage forms prepared as above are retained in the stomach and release acyclovir over a prolonged period.

EXAMPLE 1 (ASSAY)

Banded devices fabricated in Preparation 1 are assayed for dimensional changes and release of active agent as follows:

A banded dosage form is placed in a beaker of simulated gastric fluid, as specified in U.S. Pharmacopedia/National Formulary 23/18, having a pH of approximately 1.4 and a maintained temperature of 37° C. After one hour, the device is removed and measured for dimensional change in length and diameter. The swollen device will have the general appearance of the dosage form shown in FIG. 4.

Samples of the dosage form are tested for release of active agent by shaking at prescribed conditions in an aqueous media simulating the media in the upper gastrointestinal tract. Each dosage form is first placed in a cylindrical, slotted basket having inside diameter of 15 mm and inside length of 52 mm. Each basket has eight slots and each slot is 1–2 mm wide and 52 mm long and positioned lengthwise along the length of the basket. The basket containing the dosage form is then placed in 50 milliliters of simulated gastric fluid and shaken at a frequency of 100 cycles per minutes at an amplitude of 3.7 cm for one hour. Then, the baskets containing the dosage forms are transferred to another set of receptacles having the same fluid media composition and volume as above and shaken for another hour. This procedure is continued until the number of desired 50 ml release receptor samples representing the number of hours of release are accumulated. After the collective number of hours, each basket is transferred to a fresh, single 50 ml receptor where it is then shaken for an additional 3 hours. This completes the testing period. The concentration of active agent in the resulting receptors is then analyzed by using ultraviolet spectrometry assay at a wavelength specific for the active agent being tested. The release of active agent as a function of time, e.g. release rate (mg/hour), cumulative release (mg), and time for 90% release of active agent ($T_{90}$) are determined.

EXAMPLE 2

Dosage forms of this invention containing the antiviral drug ganciclovir are prepared in accordance with the procedures of Preparation 1. The dosage forms prepared are retained in the stomach and release ganciclovir over a prolonged period of time.

EXAMPLE 3

Equivalent amounts of the following polymers are substituted for the polyethylene oxide in the retention-layer in Preparation 1 (all molecular weights are number average molecular weights in grams per mole): hydroxypropyl cellulose (MW: 1,000,000), hydroxypropyl methyl cellulose (MW: 254,000), hydroxyethyl cellulose (MW: 1,300,000), sodium carboxy methylcellulose (MW: 700,000), calcium carboxymethyl cellulose (MW: 700,000), methyl cellulose (MW: 135,000), and polyvinyl alcohol (Elvanol® HV), and dosage forms with a polyethylene band are fabricated to the same dimensions as described in Preparation 1 with equivalent quantities of the active agents acyclovir and ganciclovir. The prepared dosage forms are retained in the stomach of a subject for a prolonged period and deliver the antiviral active agents ganciclovir and acyclovir over a prolonged period of time.

EXAMPLE 4

Dosage forms containing equivalent quantities of the antiviral drugs acyclovir and ganciclovir are prepared according to the procedures in Preparation 1, except that the nonwater soluble hydroattractant used is, respectively, microcrystalline cellulose (Avicel), cross-linked sodium or calcium carboxymethyl cellulose, cellulose fiber (Solka-Floc, Arbocel, Elcema), cross-linked polyvinyl pyrrolidone (Polyplasdone XL), cross-linked Amberlite resin, alginates (Satialgine), colloidal magnesium-aluminum silicate (Veegum), corn starch granules, rice starch granules, potato starch granules, and sodium carboxymethyl starch (Expotab, Primojel). The prepared dosage forms are retained in the stomach of a subject and deliver active agent over a prolonged period of time.

EXAMPLE 5

The following active agents are substituted, in the quantities indicated in the parentheses following each active agent listed, for the quantity of acyclovir in Preparation 1: cimetidine (400 mg; 800 mg, 1200 mg, 1600 mg), ranitidine (150 mg; 200 mg, 300 mg), captopril (12.5 mg; 25 mg; 50 mg; 100 mg, 150 mg), methyldopa (125; 250; 500 mg), and selegiline (5 mg, 10 mg) and the dosage forms are prepared in the same manner as described in Preparation 1. The prepared dosage forms are retained in the stomach of:a subject and deliver active agent over a prolonged period of time.

EXAMPLE 6

Dosage forms of this invention containing 600 mg of acyclovir are fabricated according to the procedures of Preparation 1, except that the tablet is inserted into a size "00" hard gelatin capsule before banding. The band is applied by a printing process using the methods and compositions described in U.S. Pat. No. 5,534,263, incorporated herein by reference, where the band material is ethyl acrylate/methyl methacrylate 70:30 copolymer applied as an aqueous latex (Eudragit NE 30 D, Rohm Tech). The banding material may be formulated with 30% by weight of a plasticizer, such as triacetin. Optionally, an amount of organic solvent such as ethyl alcohol or isopropyl alcohol may be blended into the aqueous latex to promote good band formation and rapid drying of the latex after application. The resulting dosage forms are smooth and easy to swallow.

EXAMPLE 7

A gastric platform dosage form of the antihistamine drug, fexofenadine hydrochloride, is prepared according to the following procedures. The active agent layer is prepared from 11.5 grams of the drug, 30 grams of polyethylene oxide, 54 grams of low-substituted hydroxypropyl cellulose, and 3.7 grams of polyvinyl pyrrolidone by individually passing those materials through a sieve having 40 wires per inch, and then tumble mixing the three components together for 10 minutes. The polyethylene oxide (Polyox® WSR-N-60K as supplied by Union Carbide, Danbury, Conn.) has a molecular weight of approximately 2 million grams per mole, the polyvinyl pyrrolidone (Povidone® K2932 as supplied by GAF Corporation, New York, N.Y.) has a molecular weight of approximately 45,000 grams per mole and the hydroxypropyl cellulose (LHPC-II supplied by Shin-Etsu Chemical Company, Tokyo, Japan) has a hydroxypropyl content of approximately 11 weight percent. Anhydrous ethyl alcohol formula SDA 3A is slowly added to the dry mixture with stirring until a uniform damp mass is formed. The damp mass is forced thorough a sieve with 20 wires per inch, forming elongated granules which are then air dried at ambient room conditions overnight. The resulting dried granules are then passed through the 20 mesh sieve forming more rounded granules. Then, 0.30 grams of the flow-promoting agent, colloidal. silicon dioxide (Aerosil® 200 supplied by Degussa Inc, New York, N.Y.), is dry mixed into the blend. Finally, 0.5 grams of the tableting lubricant, magnesium stearate, previously passed through a sieve having 60 wires per inch, is tumble blended into the bulk. This produced the final granulation for the active agent layer.

The highly swellable layer is prepared from 99% polyethylene oxide (Polyox 303) and 1% ferric oxide by tumble mixing those components for approximately 10 minutes. The anhydrous ethyl alcohol formula SDA 3A is slowly added to form a damp mass that is forced through a sieve with 20 wires per inch and dried overnight under ambient conditions.

Individual portions of the drug granulation weighing approximately 522 mg and of the highly swellable, retention layer granulation weighing approximately 522 mg each are separately compressed with size 0 caplet tooling on a Carver press with a force of about 1.5 tons to form a bilayer, laminated tablet core. Each tablet contains about 120 mg of fexofenadine hydrochloride.

A solution for use in film coating the tablets is then prepared by stirring 40 grams of methyl cellulose (Methocel A15 LV Premium supplied by Dow Chemical, Midland, Mich.) and 10 grams of sorbitol in 950 grams of purified water at room temperature. The mixture is chilled overnight at 9° centigrade to complete dissolution. The tablets from above are then transferred to a pharmaceutical coating pan, and spray coated with the solution in a current of warmed air until a dry film coating weight of about 37 mg is deposited onto each tablet. The film coated tablet cores are then dried in a forced air oven at 40 degrees Centigrade overnight.

An aqueous dispersion for use in banding the tablets is prepared by dissolving 30 grams of triacetin in 174.75 grams of ethyl acrylate methylmethacrylate 70:30 copolymer aqueous dispersion (Eudragit® NE40D supplied by Rohm Corporation, Darmstadt, West Germany). Then, 0.1 grams of anti-foam agent (Simethicone Q7–2587, Dow Chemical, Midland, Mich.) is blended into the mixture. This forms the final composition of the banding dispersion.

The dried film coated tablets from above are then banded by applying the above banding dispersion in a transfer printing process using a printing wheel having a width of approximately 100 mils (2.54 mm). The freshly banded system is then dried in warm air to remove the water from the aqueous dispersion, leaving a single band located in the center of the caplet having a width of approximately 120 mils (3.05 mm) and a weight of approximately 21 mg. The entire banded system is then overcoated with more of the aqueous-based film coat solution using the formulation and process as described above until a film coat weight of about 31 mg is applied. This completes fabrication of the dosage form.

EXAMPLE 8

A gastric platform dosage form delivering the antibiotic, minocylcine, for treatment of Helicobacter pylori gastritis, gastric and duodenal ulcers, with a single core layer is fabricated and compared to a bilayer core system of this invention. The procedures for fabrication are similar to those specified in EXAMPLE 7. For the single layer dosage form, 17.8 grams of minocycline hydrochloride, 24.6 gams of polyethylene oxide 53.8 grams of low-substituted hydroxypropyl cellulose, 3 grams of polyvinyl pyrrolidone 0.3 grams of colloidal silicon dioxide, and 0.5 grams of magnesium stearate are granulated according to the procedures in EXAMPLE 7. The excipients are the same as in this example except the polyethylene oxide had a molecular weight of approximately 4 million grams per mole (Polyox WSR 301). The granulation is compressed into caplets weighing approximately 1042 mg where each tablet contains a unit dose of about 185 mg of minocycline hydrochloride. The tablets are film subcoated with a coating weight of 52 mg, banded with a 21 mg band, and overcoated with 21 mg of film. The compositions of the subcoat, band, and overcoat are the same as disclosed in EXAMPLE 7.

The bilayer dosage form is prepared using the granulation procedures of EXAMPLE 7. 35.4 Grams of minocycline hydrochloride, 22.0 grams of Polyox WSR-301, 39 grams of low-substituted hydroxypropyl cellulose, 2.8 grams of polyvinyl pyrrolidone K2932 are wet granulated. 0.3 Grams of Aerosil silicon dioxide and 0.5 grams of magnesium stearate are dry mixed into the blend, producing the finished drug layer granulation. The retention layer is prepared by passing 80 grams of Polyox WSR-303 and 20 grams of powdered cellulose Solka Floc 900 (Fiber Sales and Development Corporation, Urbana, Ohio) through a 40 mesh screen and the components are tumbled mixed for about 10 minutes. Denatured ethanol formula 3A is added with stirring to form a uniform damp mass, which is then forced through a 20 mesh sieve. The resulting granules are air dried overnight, then passed again through the 20 mesh sieve, producing the high-swelling, retention layer granulation. Then, the drug layer granulation and the retention layer granulation are compressed into biayer caplets consisting of a drug layer of. 522 mg and a retention layer of 522 mg. The bilayer tablets are film coated and banded according to the compositions and procedures described in EXAMPLE 7. Each dosage form, i.e., bilayer tablet, contained 185 mg of minocycline hydrochloride.

Figure 7:
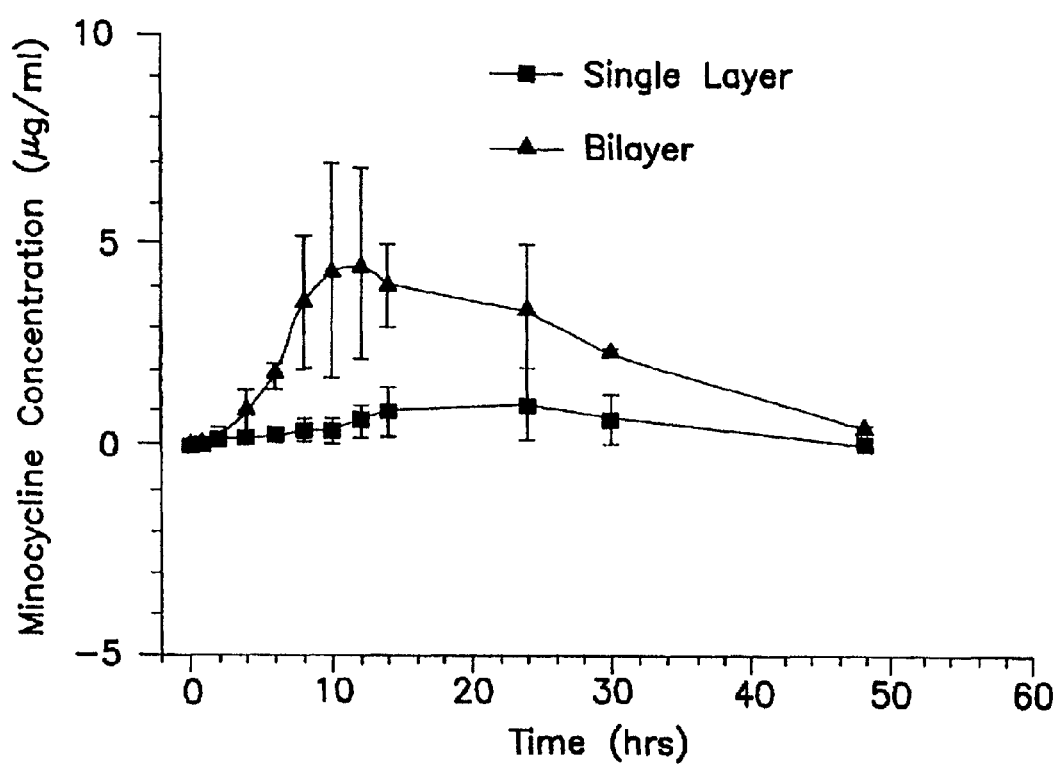
FIG. 7 illustrates a representative profiles of the concentration of minocycline in the plasma of dogs from the bilayer dosage form of the invention described in Example 8 and a mono-system, also described in Example 8, in which the drug is incorporated into the expandable layer to form a mono-system.

The resulting single layer and bilayer dosage forms are compared in vivo as follows: A single layer dosage form is administered to each of three dogs in the fed state. Plasma samples are collected periodically over the 48-hour period post dosing. The concentration of the minocycline hydrochloride in the samples is then measured by high pressure liquid chromatography and recorded. After a suitable washout period of two weeks, the bilayer dosage forms were administered to the dogs and tested under the same conditions. The results of the study are presented in FIG. 7. The square symbols depicted in the graph correspond to the plasma concentration profile of drug generated by the single layer dosage form and the triangular symbols s correspond to the plasma concentration profile of drug generated by the bilayer dosage form. The bilayer dosage form exhibits a multifold increase in drug bioavailability (as measured by the area under the curve; "AUC") and a more elevated plasma concentration compared to the single layer dosage form without the retention layer. The calculated AUC of the bilayer dosage form was 119±26 μg hr/ml and the calculated AUC of the monolayer dosage forms was 28.1±21 μg hr/ml.

EXAMPLE 9

Figure 8A:
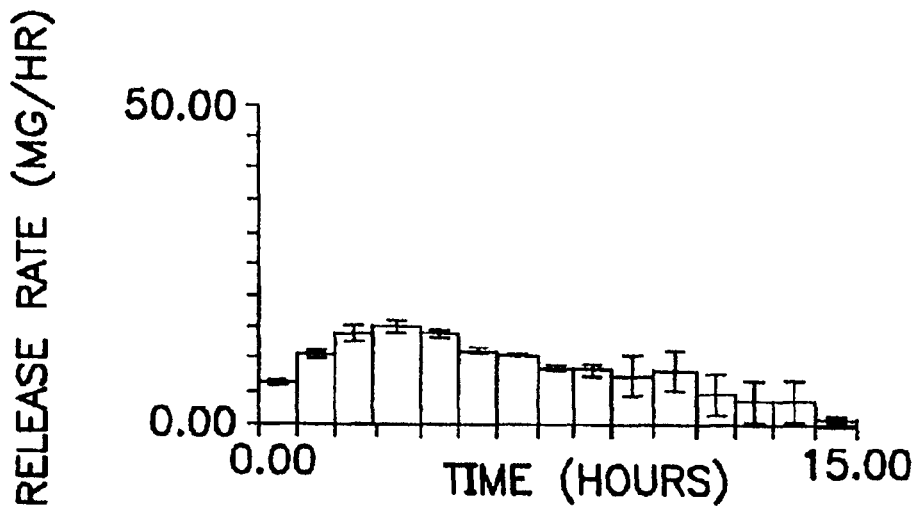
FIGS. 8A and 8B illustrate a representative in vitro release rate profile and the corresponding cumulative release, respectively, for the drug fexofenadine hydrochloride from a form of the invention illustrated in FIG. 1 in which the retention layer is prepared from Polyox 303 and the drug layer is prepared from Polyox WSR N-60K and low substituted hydroxypropylcellulose.
Figure 8B:
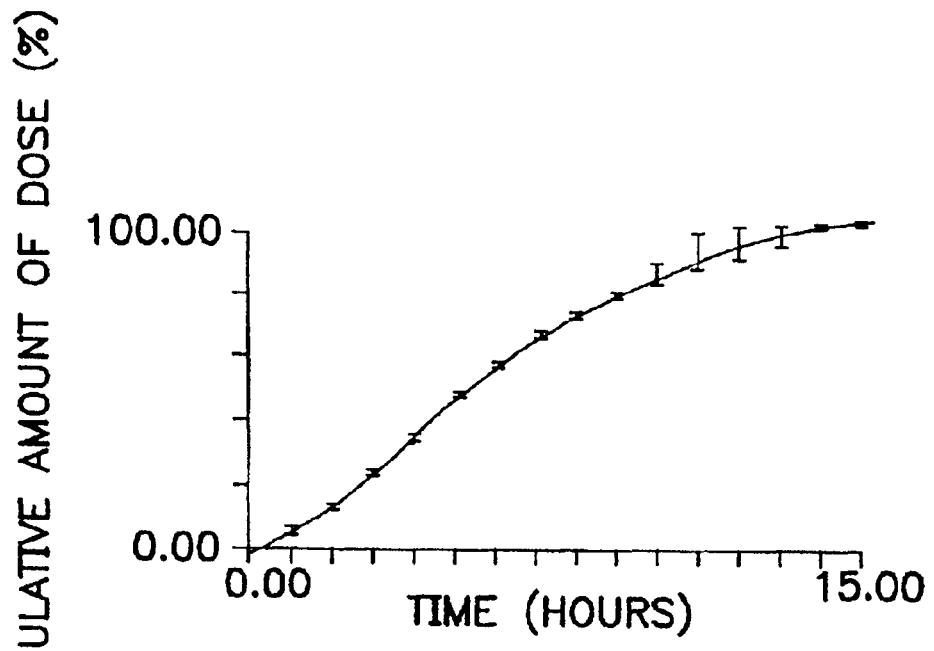

Dosage forms of the invention are prepared in accordance with the procedure of Example 7 having the following components and composition (all percentages are weight percent): The active agent layer (522 mg) contains 23% fexofenadine hydrochloride, 24.2% of Polyox WSR N-60K, 50% LHPC (low substituted hydroxypropylcellulose), 2% polyvinylpyrrolidone (PVPK 2932), 0.3% silicon dioxide (Aerosil 200) and 0.5% magnesium stearate. The highly-swellable layer (522 mg) contains 99% Polyox 303 and 1% red ferric oxide. The first overcoat (33 mg) contains 80% Methocel Al5LV Premium and 20% sorbitol. The banding material (21 mg) contains 69.9% Eudragit NE 40D (dry weight basis), 30% triacetin and 0.1% simethicone Q7-2587. The final overcoat (28 mg) contains 80% Methocel A15LV and 20% sorbitol. The release rate and cumulative release for representative dosage forms is presented in FIGS. 8A and 8B, respectively. The dosage forms exhibit a mean release rate of about 10.4 mg/hour and a $T_{90}$, time to deliver, 90% of the amount of active agent in the dosage form, of about 10.3 hours.

EXAMPLE 10

Figure 9A:
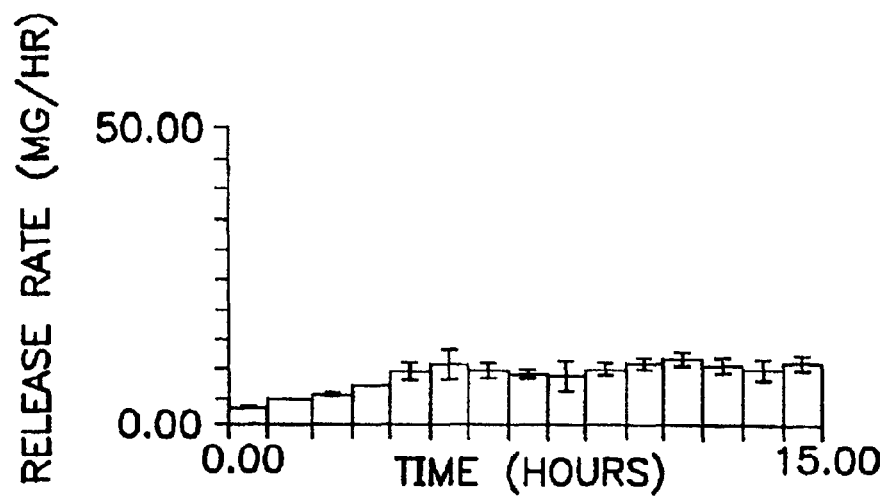
FIGS. 9A and 9B illustrate a representative in vitro release rate profile and the corresponding cumulative release, respectively, for the drug fexofenadine hydrochloride from a form of the invention illustrated in FIG. 1 in which the retention layer is prepared from Polyox 303 and the drug layer is prepared from Polyox WSR 301K and low substituted hydroxypropylcellulose.
Figure 9B:
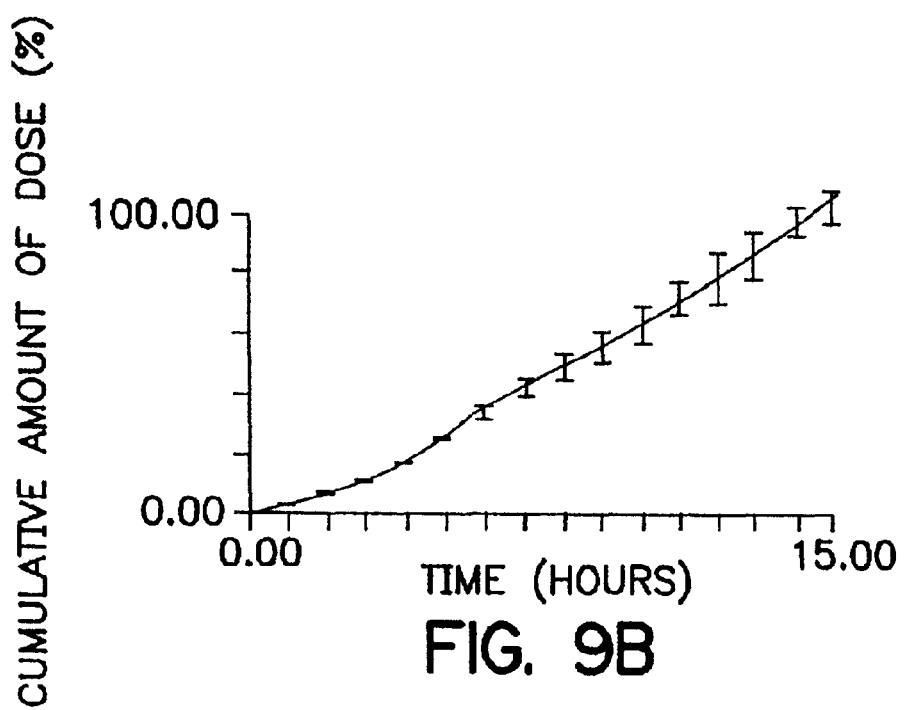

Dosage forms are prepared in accordance with Examples 7 and 9 except that Polyox 301K is substituted for the Polyox WSR N-60K in the drug layer. The release rate and cumulative release of fexofenadine hydrochloride is presented in FIGS. 9A and 9B respectively. Representative dosage forms exhibit a mean release rate of about 7.4 mg/hour and a $T_{90}$ of about 13.8 hours.

EXAMPLE 11

This example illustrates the identification and evaluation of compositions of the high-swelling layer. Formulation 1 was prepared by passing 25 grams of polyethylene oxide and 25 grams of cellulose fiber through a sieve with 4 wires per inch. The resulting mixture was tumble mixed in a V-blender for 10 minutes. The polyethylene oxide had a molecular weight of approximately 7 million grams per mole (Polyox 303). The cellulose fiber had an average fiber length of 110 microns and is supplied under the trade name SOLKA-FLOC 900FCC. The mixed powders were then transferred to a beaker where anhydrous ethyl alcohol formula SDA3 A was added with stirring to form a uniform damp mass. The resulting damp mass was forced through a sieve with 20 wires per inch, producing elongated granules. The granules were then air dried overnight at ambient room conditions. The resulting dried granules were then forced with a spatula through the 20-mesh sieve to produce Granulation 1. A portion of Granulation 1 weighting 1.04 grams was filled into a punch and die set mounted on a Carver press. The tooling was caplet shaped, with major axis dimension of 0.85 inch (21.6 mm) and a minor axis dimension of 0.3 inch (7.6 mm). The caplet was compressed using a pressure head of 1.5 tons.

The swelling properties of the resulting caplet 1 were then evaluated in vitro. The caplet was placed in 900 ml of simulated gastric fluid therostated at 37° C. The gastric fluid had a pH value of 1.2 and was prepared according to the formula, but without enzyme, as specified in the US Pharmacopeia 23/National Formulary 18, page 2053. The compact was tested in this fluid using the paddle test apparatus described on page 1792 of the same reference. The paddle speed was maintained at 212 revolutions per minute to simulate mechanical insult and abrasion in vivo in the environment of use. After 30 minutes of testing in these conditions, the caplet was removed. The dimension of the minor axis was measure using an optical inspection system (RAM Optical Instrumentation, Huntington Beach, Calif.). The percent increase in the minor axis dimension was then calculated. The swollen caplet was then returned to the testing bath. After another 30 minutes in the bath under test conditions, the caplet was removed and the dimensions were again measured and the percent increase in the minor axis was again calculated. Each calculation was based o the dimension of minor axis at time zero, i.e., 7.6 mm. This process was continued hourly for the next four hours. The percent increase in minor axis dimension was plotted as a function of test time and the results are represented by the diamond-shaped symbols in FIG. 10.

Three other caplets having different compositions were prepared and tested according to the procedures described above. Formulation 2 consisted of 25 grams of Polyox 303, 12.5 grams of Solka-Floc 900FCC, and 12.5 grams of sodium chloride. The dimensional changes of this caplet as a function of time are represented by hexagonal symbols in FIG. 10. The rate and extent of swelling of Formulation 1 and Formulation 2 were similar. Both increased in minor axis dimension by about 75% at a time of one hour and both swelled to about 140% by a time of 5 hours. Formulation 2 had a higher bulk density than Formulation 1 and flowed and filled die cavities more quickly, thus making it preferable for use in high speed tableting operations.

Figure 10:
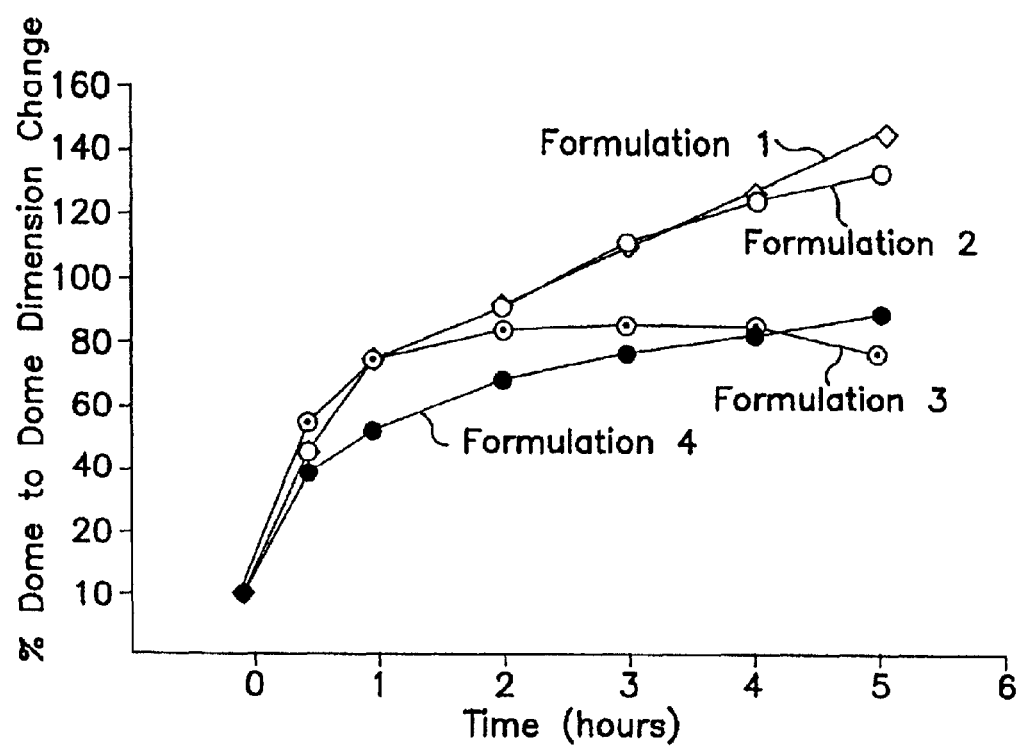
FIG. 10 illustrates the dimensional changes as measured by in vitro testing of the swelling of various formulations of the high-swelling layer of the dosage forms of the invention.

Formulation 3 consisted of 25 grams of Polyox 303 and 25 grams of sodium chloride. The results of swelling of the caplet formed of this formulation is illustrated in FIG. 10 by the open circular symbols. Swelling of this caplet at one hour was comparable to that of Formulations 1 and 2, but this caplet did not swell to the extent of the caplets formed from Formulations 1 and 2 at the end of the five hour period. Formulation 4 consisted of 50 grams of Polyox 303. Swelling behavior of the caplet of this granulation is represented by the curve with the closed circles in FIG. 10. Formulation 4 swelled more slowly and to a lesser extent than Formulations 1 and 2. The results demonstrate that the presence of cellulosic fibers increases the rate and extent of the swelling process over formulations that do not include the fibers. Also, the presence of the sodium chloride provides a granulation bulk density that is more suitable for high speed tableting processes than formulations without the sodium chloride.

The present invention is described and characterized by one or more of the following technical features and/or characteristics, either alone or in combination with one or more of the other features and characteristics: an active agent dosage form adapted for gastric retention comprising: (a) a first layer comprising a swellable, water-soluble polymer; (b) a second layer comprising a therapeutically-effective amount of an active agent, the second layer being laminated with the first layer at a common surface, and (c) at least one band of insoluble material circumscribing and binding together the first layer and the second layer, the first layer being adapted to swell in the stomach to facilitate retention of the dosage form in the stomach over a prolonged period of time, wherein the release of the active agent from the second layer is independent of the composition of the first layer and occurs over a prolonged period of time; a dosage form wherein the number average molecular weight of the water-soluble polymer is between about 100,000 and 20,000,000 grams per mole; a dosage form wherein the water soluble polymer is polyethylene oxide, hydroxypropyl cellulose, hydroxypropyl methyl cellulose, hydroxyethyl cellulose, sodium carboxy methylcellulose, calcium carboxymethyi cellulose, methyl cellulose, polyacrylic acid, maltodextrin, pre-gelatinized starch, guar gum, sodium alginate, or polyvinyl alcohol; a dosage form wherein the second layer comprises a hydroattractant selected from low-substituted hydroxypropyl cellulose, microcrystalline cellulose, cross-linked sodium or calcium carboxymethyl cellulose, cellulose fiber, cross-linked polyvinyl pyrrolidone, cross-linked polyacrylic acid, cross-linked Amberlite resin, alginates, colloidal magnesium-aluminum silicate, corn starch granules, rice starch granules, potato starch granules and sodium carboxymethyl starch, and the first layer optionally comprises a hydroattractant selected from low-substituted hydroxypropyl cellulose, microcrystalline cellulose, cross-linked sodium or calcium carboxymethyl cellulose, cellulose fiber, cross-linked polyvinyl pyrrolidone, cross-linked polyacrylic acid, cross-linked Amberlite resin, alginates, colloidal magnesium-aluminum silicate, corn starch granules, rice starch granules, potato starch granules and sodium carboxymethyl starch; a dosage form wherein the first layer swells more rapidly and to a greater extent than does the second layer; a dosage form wherein the active agent is an antiviral, antimicrobial, antidiabetic, antihyperglycemic, hypoglycemic, antidepressant, antiobesity or antifungal active agent; a dosage form wherein the weight percent of the water soluble polymer in the second layer is 5 to 99.99 weight percent and weight percent of the hydroattractant in the second layer is 0 to 60 weight percent; a dosage form wherein the prolonged time period is at least 3 hours; a dosage form wherein the prolonged time period is between about 6 to 12 hours; a dosage form wherein the first layer comprises polyethylene oxide having a number average molecular weight of at least 100,000 grams per mole; a dosage form wherein the active agent is acyclovir, ganciclovir, ritonavir, minocycline, cimetidine, ranitidine, captopril, methyldopa, selegiline, minocycline, fexofenadine, metformin, bupropion, orlistat or a pharmaceutically acceptable salt thereof; a dosage form wherein the second layer comprises an active agent selected from the group consisting of acyclovir, ganciclovir, ritonavir, metformin, bupropion, orlistat and minocycline, and the second layer comprises a bioerodible polymer, a therapeutically effective amount of the active agent being delivered to the stomach of a subject over at least a 3 hour period; a method of treating a subject in need thereof with an active agent that comprises administering to the subject a multilayered dosage form adapted to be retained in the stomach over a prolonged period of time, the dosage form comprising a second layer adapted to swell in the stomach of the subject and retain the dosage form in the stomach for a prolonged period of time, and a first layer adapted to deliver to the subject an active agent at a variable rate of delivery; a method which comprises administering one or more dosage forms to the subject in the fed state at the start of each dosing period; a method wherein the administration of the dosage form occurs within one hour of the subject consuming food; a dosage form comprising a gastric-emptying delaying agent; a dosage form wherein the gastric-emptying delaying agent is selected from anticholinergic agents, methylcellulose, guar gum, fats and fatty acids of 10–15 carbon atoms; a dosage form wherein the active agent comprises a liquid, active agent formulation; a dosage form wherein the liquid, active agent formulation is sorbed into porous particles; a dosage form wherein the porous particles are calcium hydrogen phosphate or magnesium alumi-nometasilicate; a dosage form comprising a pH regulating agent or a chelating agent; a dosage form wherein the liquid, active agent formulation comprises a pH regulating agent selected from organic and inorganic acids and bases, a dosage form wherein the liquid, active agent formulation comprises a chelating agent.

The above description has been given for ease of understanding only. No unnecessary limitations should be understood therefrom, as modifications will be obvious to those skilled in the art.

What is claimed is:

1. An active agent dosage form comprising:
    a first layer comprising an amount of swellable polymer, said amount being sufficient to swell said first layer such that the active agent dosage form is retained within a stomach of a subject;
    a second layer laminated with the first layer at a common surface, said second layer comprising a therapeutic amount of an active agent and being formulated to swell to a lesser extent than the first layer; and
    at least one band of insoluble material circumscribing only a portion of said first layer and said second layer, said at least one band of insoluble material binding together the first layer and the second layer.

2. The active agent dosage form of claim 1, wherein the number average molecular weight of the swellable polymer is between about 100,000 and 20,000,000 grams per mole.

3. The active agent dosage form of claim 2, wherein the swellable polymer is polyethylene oxide, hydroxypropyl cellulose, hydroxypropyl methyl cellulose, hydroxyethyl cellulose, sodium carboxy methylcellulose, calcium carboxymethyl cellulose, methyl cellulose, polyacrylic acid, maltodextrin, pre-gelatinized starch, guar gum, sodium alginate, or polyvinyl alcohol.

4. The active agent dosage form of claim 1, wherein the second layer comprises a hydroattractant selected from low-substituted hydroxypropyl cellulose, microcrystalline cellulose, cross-linked sodium or calcium carboxymethyl cellulose, cellulose fiber, cross-linked polyvinyl pyrrolidone, cross-linked polyacrylic acid, a cross-linked ion exchange resin, alginates, colloidal magnesium-aluninum silicate, corn starch granules, rice starch granules, potato starch granules, sodium carboxymethyl starch, sugars, and sodium chloride, and the first layer optionally comprises a hydroattractant selected from low-substituted hydroxypropyl cellulose, microcrystalline cellulose, cross-linked sodium or calcium carboxymethyl cellulose, cellulose fiber, ctoss-linked polyvinyl pyrrolidone, cross-linked polyacrylic acid, cross-linked ion exchange resin, alginates, colloidal magnesium-aluminum silicate, corn starch granules, rice starch granules, potato starch granules, sodium carboxym ethyl starch, sugars and sodium chloride.

5. The active agent dosage form of claim 1, wherein the first layer swells more rapidly than does the second layer.

6. The active agent dosage form of claim 1, wherein the active agent is an antiviral, antimicrobial antidiabetic, antihyperglycemic, hypoglycemic, antidepressant, antiobesity or antifungal active agent.

7. The active agent dosage form of claim 1, wherein the second layer includes 5 to 99.99 weight percent of a swellable polymer and further includes up to 60 weight percent, inclusive, of a hydroattractant.

8. The active agent dosage form of claim 1, wherein the first layer is formulated such that the active agent dosage form is retained within the stomach for a prolonged period of time.

9. The active agent dosage form of claim 8, wherein the prolonged period of time is at least 3 hours.

10. The active agent dosage form of claim 1, wherein the first layer is formulated such that the active agent dosage form is retained within the stomach for between about 6 to 12 hours.

11. The active agent dosage form of claim 1, wherein the first layer comprises polyethylene oxide having a number average molecular weight of at least 100,000 grams per mole.

12. The active agent dosage form of claim 11, wherein the active agent is an antiviral, antimicrobial, antidiabetic, antihyperglycemic, hypoglycemic, antidepressant, antiobesity or antifungal active agent.

13. The active agent dosage form of claim 12, wherein the active agent is acyclovir, ganciclovir, ritonavir, minocycline, cimetidine, ranitidine, captopril, methyldopa, selegiline, minocycline, fexofenadine, metformin, bupropion, orlistat or a pharmaceutically acceptable salt thereof.

14. The active agent dosage form of claim 11, wherein the active agent is metformin or a pharmaceutically acceptable salt thereof.

15. The active agent dosage form of claim 1, wherein the second layer comprises an active agent selected from the group consisting of acyclovir, ganciclovir, ritonavir, metformin, bupropion, orlistat and minocycline, and the second layer comprises a bioerodible polymer, wherein the dosage form is formulated to release a therapeutically-effective amount of the active agent to the stomach of a subject over at least a 3 hour period.

16. A method for treating a subject in need thereof with an active agent, the method comprising:
    administering to the subject a multilayered dosage form which is retained in a stomach of the subject over a prolonged period of time, the dosage form comprising:
        a first layer comprising an amount of swellable polymer, said amount being sufficient to swell said first layer such that said active agent dosage form is retained within the stomach of a subject;
        a second layer laminated with the first layer at a common surface, said second layer comprising a therapeutic amount of an active agent and being formulated to swell to a lesser extent than the first layer; and
        at least one band of insoluble material circumscribing only a portion of said first layer and said second layer, said at least one band of insoluble material binding together the first layer and the second layer.

17. The method of claim 16, which comprises administering one or more of the multilayered dosage forms to the subject in the fed state at the start of each dosing period.

18. The method of claim 17, wherein the administration of one or more of the multi-layered dosage forms occurs within one hour of the subject consuming food.

19. The active agent dosage form of claim 1, further comprising a gastric-emptying delaying agent.

20. The active agent dosage form of claim 19, wherein the gastric-emptying delaying agent is selected from anticholinergic agents, methylcellulose, guar gum, fats and fatty acids of 10–15 carbon atoms.

21. The active agent dosage form of claim 1, wherein the active agent comprises a liquid active agent formulation.

22. The active agent dosage form of claim 21, wherein the liquid active agent formulation is sorbed into porous particles.

23. The active agent dosage form of claim 22, wherein the porous particles are calcium hydrogen phosphate or magnesium aluminometasilicate.

24. The active agent dosage form of claim 1, wherein the dosage form comprises a pH regulating agent.

25. The active agent dosage form of claim 22, wherein the liquid active agent formulation comprises a pH regulating agent selected from organic and inorganic acids and bases.

26. The active agent dosage form of claim 22, wherein the liquid active agent formulation comprises a chelating agent.

* * * * *